(12) United States Patent
Schiestle et al.

(10) Patent No.: US 11,801,511 B2
(45) Date of Patent: Oct. 31, 2023

(54) ERGONOMIC STOOL SPECIMEN CONTAINER AND ENCLOSING HOLDER SYSTEMS, METHODS, AND KITS

(71) Applicant: Exact Sciences Corporation, Madison, WI (US)

(72) Inventors: Joseph E. Schiestle, Madison, WI (US); Krystal A. Burger, Lake St. Croix Beach, MN (US); Timothy A. Parmer, St. Paul, MN (US); Jad A. Lunde, Bay City, WI (US); Sam M. Jang, Woodbury, MN (US); David A. Schuelke, Hudson, WI (US); David B. Wolgemuth, Elk Mound, WI (US); Jing Yang Lu, Madison, WI (US)

(73) Assignee: Exact Sciences Corporation, Madison, WI (US)

( * ) Notice: Subject to any disclaimer, the term of this patent is extended or adjusted under 35 U.S.C. 154(b) by 404 days.

(21) Appl. No.: 17/091,951

(22) Filed: Nov. 6, 2020

(65) Prior Publication Data

US 2021/0162400 A1    Jun. 3, 2021

Related U.S. Application Data

(60) Division of application No. 16/276,185, filed on Feb. 14, 2019, now Pat. No. 10,894,256, which is a
(Continued)

(51) Int. Cl.
*B01L 3/00* (2006.01)
*G01N 1/38* (2006.01)
*A61B 10/00* (2006.01)

(52) U.S. Cl.
CPC .......... *B01L 3/508* (2013.01); *B01L 3/50825* (2013.01); *G01N 1/38* (2013.01); *A61B 10/0038* (2013.01);
(Continued)

(58) Field of Classification Search
CPC ................ B01L 3/508; B01L 3/50825; B01L 2200/0689; B01L 2200/087;
(Continued)

(56) References Cited

U.S. PATENT DOCUMENTS

| 2,796,188 A | 6/1957 | Kurkjian |
| 4,101,279 A | 7/1978 | Aslam |

(Continued)

FOREIGN PATENT DOCUMENTS

| WO | WO 2005/014154 | 2/2005 |
| WO | WO 2009/150881 | 12/2009 |
| WO | WO 2015/031832 | 3/2015 |

OTHER PUBLICATIONS

International Search Report and Written Opinion for PCT/US2014/053542, dated Dec. 18, 2014, 15 pages.
(Continued)

*Primary Examiner* — Samuel P Siefke
(74) *Attorney, Agent, or Firm* — Casimir Jones, S.C.; Mary Ann D. Brow

(57) ABSTRACT

Provided herein is technology relating to collecting and containing samples and particularly, but not exclusively, to technology for collecting and containing a stool specimen. The technology provides a device for collecting and containing a stool specimen, the device comprising ergonomic features optimized for a geriatric user. The technology also provides an enclosing holder for securing the ergonomic stool specimen container in a leak-proof manner e.g., during mechanical shaking.

11 Claims, 30 Drawing Sheets

Related U.S. Application Data continuation of application No. 14/914,453, filed as application No. PCT/US2014/053542 on Aug. 29, 2014, now Pat. No. 10,265,054.

(60) Provisional application No. 61/871,702, filed on Aug. 29, 2013.

(52) U.S. Cl.
CPC ... *A61B 10/0096* (2013.01); *B01L 2200/0689* (2013.01); *B01L 2200/087* (2013.01); *B01L 2200/185* (2013.01); *B01L 2300/042* (2013.01); *B01L 2300/043* (2013.01); *B01L 2300/0832* (2013.01); *B01L 2300/0858* (2013.01); *B01L 2300/12* (2013.01); *G01N 2001/386* (2013.01)

(58) Field of Classification Search
CPC ......... B01L 2200/185; B01L 2300/042; B01L 2300/043; B01L 2300/0832; B01L 2300/0858; B01L 2300/12; G01N 1/38; G01N 2001/386; A61B 10/0038; A61B 10/0096

See application file for complete search history.

(56) References Cited

U.S. PATENT DOCUMENTS

| | | |
|---|---|---|
| 4,288,316 A | 9/1981 | Hennessy |
| 4,603,784 A | 8/1986 | Chang |
| 4,818,114 A | 4/1989 | Ghavi |
| 4,859,610 A | 8/1989 | Maggio |
| 4,964,509 A | 10/1990 | Insley et al. |
| 5,328,043 A | 7/1994 | Ray |
| 5,624,554 A | 4/1997 | Faulkner et al. |
| 6,616,000 B1 | 9/2003 | Renz |
| 6,780,160 B2 | 8/2004 | Zhou et al. |
| 8,287,821 B2 | 10/2012 | Nakahana et al. |
| 8,322,913 B2 | 12/2012 | Galowina et al. |
| 10,265,054 B2 | 4/2019 | Schiestle et al. |
| 2002/0139767 A1 | 10/2002 | Budd |
| 2002/0195471 A1 | 12/2002 | Nottingham et al. |
| 2004/0019295 A1 | 1/2004 | Zhou et al. |
| 2005/0112024 A1 | 5/2005 | Guo et al. |
| 2006/0115385 A1 | 6/2006 | Meyer et al. |
| 2007/0151212 A1 | 7/2007 | Mayer et al. |
| 2008/0286831 A1 | 11/2008 | Liang |
| 2009/0004058 A1 | 1/2009 | Liang et al. |
| 2011/0085951 A1 | 4/2011 | Nakahana et al. |
| 2011/0107855 A1 | 5/2011 | Motadel |
| 2011/0177931 A1 | 7/2011 | Kelland et al. |
| 2012/0288956 A1 | 11/2012 | Ahlquist et al. |
| 2014/0017720 A1* | 1/2014 | Sidorsky .................. A61J 1/00 435/309.1 |
| 2019/0175153 A1 | 6/2019 | Schiestle et al. |

OTHER PUBLICATIONS

Extended European Search Report for EP 14841123, dated Jul. 21, 2017, 11 pages.

* cited by examiner

FIG. 2A
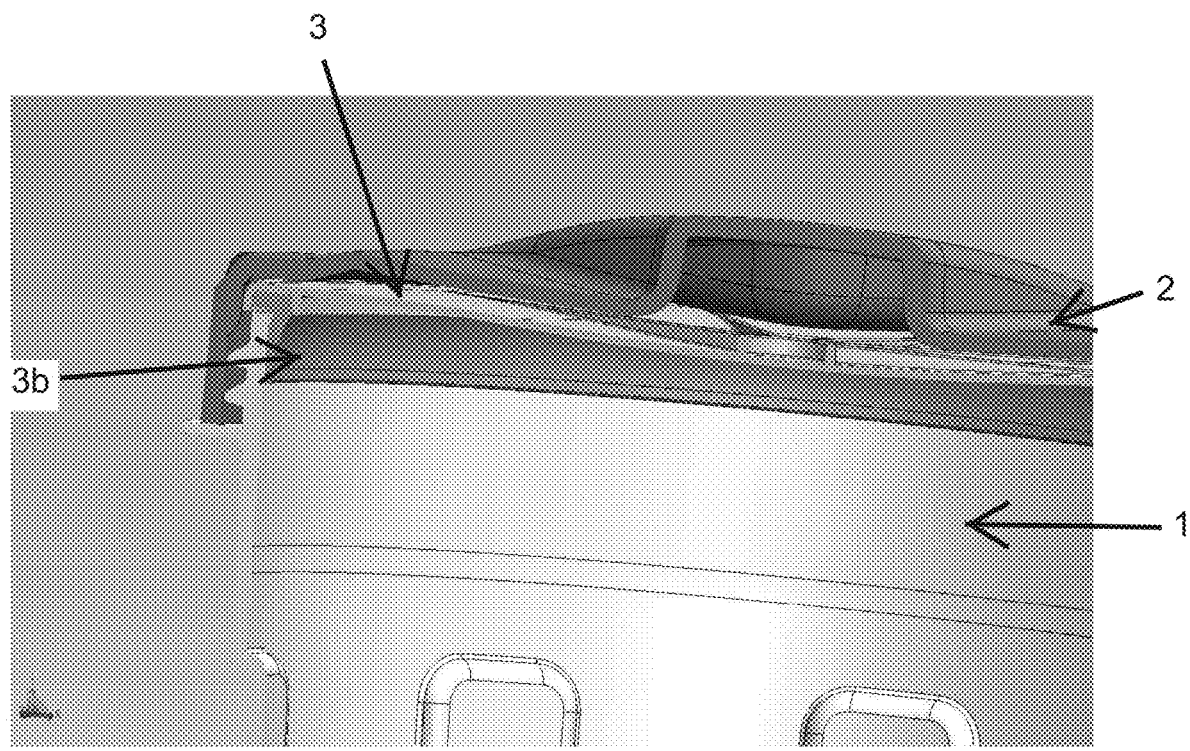
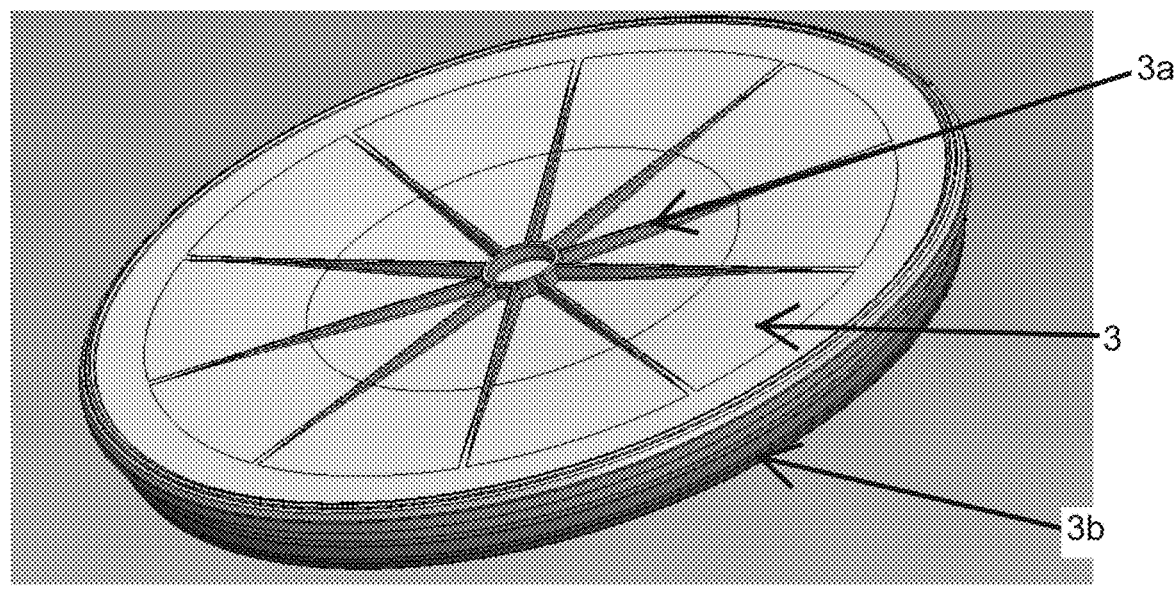
FIG. 2B

A.

B.

C.

A.

B.

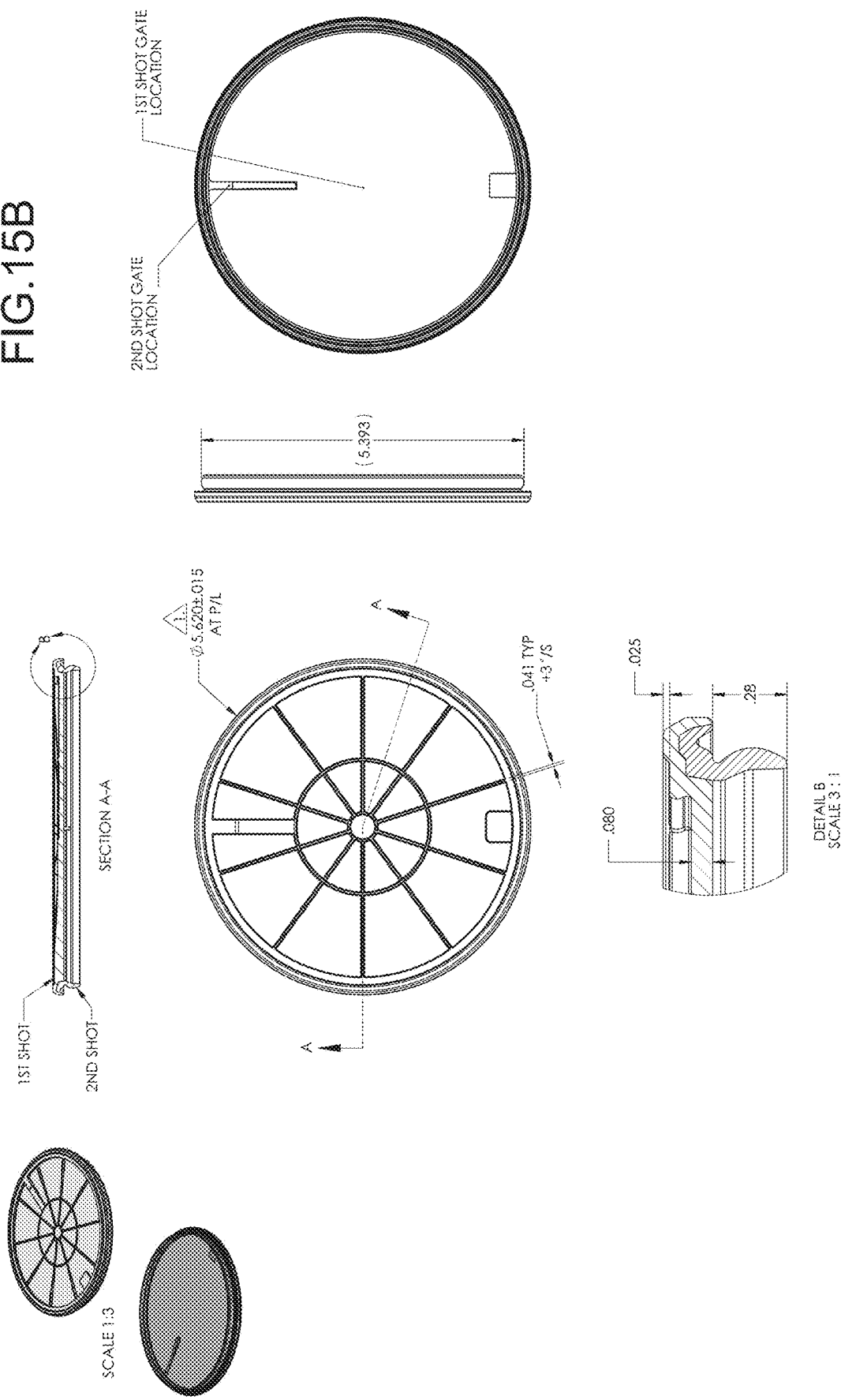

A.

B.

A.

B.

C.

D.

ERGONOMIC STOOL SPECIMEN CONTAINER AND ENCLOSING HOLDER SYSTEMS, METHODS, AND KITS

This application is a divisional of U.S. patent application Ser. No. 16/276,185, filed Feb. 14, 2019, which is a continuation of U.S. patent application Ser. No. 14/914,453, filed Jun. 15, 2016, now U.S. Pat. No. 10,265,054, which claims the benefit of U.S. Provisional Application Ser. No. 61/871,702, filed Aug. 29, 2013, each of which is incorporated herein in its entirety.

FIELD OF INVENTION

Provided herein is technology relating to collecting samples and particularly, but not exclusively, to technology for collecting a stool specimen, and to systems and methods for processing collected stool specimens.

BACKGROUND

In the medical clinic, laboratory examination of fecal samples is an important component of some diagnoses. In these cases, stool specimens are taken from a patient and examined for conditions relative to the ailment of the patient. As specific examples, physicians and clinicians often test stool samples as a component of testing for colon or rectal cancer or to identify bacteria or viruses that may be involved in an infection. Additionally, some diagnostics require isolating and assaying nucleic acids, proteins, fats, or other analytes present in a stool sample. Consequently, acquiring a specimen for testing (e.g., a stool specimen) is the first step in sample processing for many tests (e.g., the medical diagnostic analysis of feces). For samples collected by the patient, e.g., in their home, a container holding the collected sample must be suitable not only for storage of the sample until it is received in the lab, but also for transport and/or shipping of the sample to the lab where it will be examined.

Acquiring the stool specimen presents several challenges relating to, e.g., providing containers of sufficient size to receive and contain an entire sample, wherein the container is configured for handling and use by patients with different sizes of hands (e.g., small to large) and with varying degrees of hand strength, upper body strength, and/or fine motor skill and visual acuity. Patients over the age of about 50 years are particularly likely to be subject to screening methods requiring collection of stool specimens, and are also more likely have impairments in both hand usage (e.g., due to arthritis) and vision (e.g., age-related presbyopia, cataracts, macular degeneration). The likelihood of such impairments increases in older populations, e.g., in populations of geriatric patients.

Sample containers are available for collection of larger medical samples. Examples include the Collection Kit used in Exact Sciences' DeeP C Clinical Trial, as well as Collection Kits used by the Mayo Clinic and commercially available sample containers. However, prior container solutions fail in one or more of the following areas:

They are expensive for a high-volume home-based sample collection;

They are unable to withstand shipment by air or meet IATA (International Air Transportation Assoc.) regulations;

They are difficult to manipulate, and particularly to properly close and seal, especially for geriatric patients;

They experience leakage during shipment.

Conventional solutions comprise designs that are awkward to use. For example, containers sized to hold a complete stool specimen are typically of sufficient diameter that people with small or weak hands have difficulty gripping the container and/or the lid of the container, e.g., for opening, closing, and/or sealing. As a consequence, extant solutions present a significant risk of the user contaminating the sample or touching the unused stool portion when attempting disposal. Accordingly, improved devices are required that allow for the comfortable acquisition of a stool specimen, that are easy to use for the subjects providing stool specimens, that include features ensuring proper sealing, e.g., to prevent leakage during handling or shipping.

SUMMARY

The present invention provides an ergonomic container for collection, containment, shipping, and/or mixing of a stool sample, comprising certain features designed for ease of use by a human subject. Additional embodiments will be apparent to persons skilled in the relevant arts based on the teachings contained herein. The invention further provides an enclosing holder configured to contain and support an ergonomic container comprising a stool during further processing, and to reinforce the sealing of the container e.g., during shaking, rotating, gyroscopic mixing, or other mixing agitation.

In some embodiments, the present invention provides a device for containing a stool specimen, the device comprising a bucket, a lid, and a seal, wherein said bucket comprises a top edge defining a top surface, an interior side defining a circumferential vertical surface, an exterior having a gripping feature, and a first engagement portion; wherein said lid comprises a top comprising gripping feature, and a mated engagement portion adapted to removeably engage with the first engagement portion of the bucket, and wherein the seal is configured to seal the junction between the bucket and the lid when the first engagement portion of the bucket and the mated engagement portion of the lid are engaged, and wherein the seal is configured to travel independently of the bucket and the lid during manipulation to engage said first engagement portion and said mated engagement portion.

In preferred embodiments, it is contemplated that the lid provides complete coverage of the top of the bucket, e.g., that there is no hole or opening in the lid. In certain embodiments, the lid completely covers the seal when the lid is engaged with the bucket. An exemplary lid of this design in shown in FIG. 1.

In certain embodiments, the bucket has an internal volume of at least 300 ml, and in preferred embodiments, said bucket has an internal volume between about 300 ml and about 1400 ml, or any In certain embodiments, the bucket has an opening that is at least as wide as the height of the bucket. In some embodiments, the diameter of the opening (e.g., the internal diameter, ID), is greater than or equal to the height of the bucket.

As used herein, the term "interior diameter" (ID) as applied to the bucket at any level (e.g., top, bottom, midheight) refers to the maximum diameter at that level in the bucket. For example, the ID at the bottom of the bucket refers to the maximum diameter between the outer walls of the bucket, not reduced by the height of any interior features such as sample disruption bumps or ridges. In certain embodiments, the ID at the top of the bucket is the widest ID of the bucket, i.e., the bucket does not have a shoulder below the opening. In some embodiments, the ID at the bottom of the bucket is the same as the ID at the top of the bucket, and in preferred embodiments, the ID at the bottom of the bucket is smaller than the ID at the top of the bucket. In particularly preferred embodiments, the ID at the bottom of the bucket is the smallest ID of the bucket.

In some embodiments, the seal comprises a floating plate comprising a bottom horizontal surface, wherein when the first engagement portion of the bucket and the mated engagement portion of the lid are engaged, the bottom horizontal surface of the floating plate is perpendicular to the circumferential vertical surface of the bucket.

In certain preferred embodiments, the bottom horizontal surface of the floating plate comprises a compressible seating surface configured to contact the top surface of the bucket, wherein the compressible seating surface is compressed when the first engagement portion of the bucket and the mated engagement portion of the lid are engaged. In some embodiments, the floating plate comprises a cupped horizontal surface.

In some embodiments, the bottom horizontal surface of the floating plate comprises a vertical component configured to contact the circumferential vertical surface of the bucket, and to form a circumferential seal with the circumferential vertical surface when the first engagement portion of the bucket and the mated engagement portion of the lid are engaged.

In preferred embodiments, the floating plate forms a seal between the lid and both the top surface and the circumferential vertical surface of the bucket, e.g., when the first engagement portion of the bucket and the mated engagement portion of the lid are engaged.

In some embodiments, the floating plate comprises an upper horizontal surface, wherein the upper horizontal surface is disposed toward the lid when the first engagement portion of the bucket and said mated engagement portion of the lid are engaged.

In some embodiments, the upper horizontal surface of said floating plate comprises at least one raised feature, wherein said raised feature contacts the lid when the first engagement portion of said bucket and said mated engagement portion of said lid are engaged. In some embodiments, the at least one raised feature provides substantially all of the contact between the upper horizontal surface of the floating plate and the lid, when the first engagement portion of the bucket and the mated engagement portion of the lid are engaged.

In certain preferred embodiments, the device is ergonomically designed, for ease of proper use by the person collecting a stool specimen. In preferred embodiments, the ergonomic design features comprise features relating to the manipulation required to seal the container, and features designed to improve the ability of a user to manipulate the device a so as to engage the lid and bucket.

In some embodiments, manipulation to engage the first engagement portion of the bucket with said mated engagement portion of the lid comprises turning the lid with respect to said bucket. In preferred embodiments, this manipulation comprises turning the lid with respect to the bucket no more than 180 degrees, preferably no more than 90 degrees, more preferably less than 90 degrees.

The device is not limited to particular means of engaging the lid with the bucket. For example, in some embodiments, the first engagement portion comprises a first threaded portion and the mated engagement portion comprises a mated threaded portion, while in other embodiments, the first engagement portion comprises a first bayonet mount portion and the mated engagement portion comprises a mated bayonet mount portion. In yet other embodiments, the first engagement portion comprises a first snap portion and the mated engagement portion comprises a mated snap portion. In still further embodiments, multiple means of engagement are used. In some embodiments, the bucket comprises a second engagement portion, and the lid comprises a second mated engagement portion. For example, in some embodiments, the second engagement portion is a snap portion and the second mated engagement portion is a snap portion.

In some embodiments, the lid features ergonomic design features. For example, in preferred embodiments, the gripping feature(s) on the lid are configured for ease of use by a patient with, e.g., weak or small hands. In some embodiments, the gripping feature on the lid is a crossed gripping feature, e.g., as shown in FIG. 1, or in FIGS. 6a and 6c. The cross configuration is not limited to right angle-cross shapes but may include, e.g., shapes that comprise an odd or even number of graspable components (e.g., 3, 4, 5, 6, etc.) that extend from a central point or crossing point on the lid, e.g., in a radial-type configuration. In preferred embodiments, the cross configuration comprises four graspable components disposed radially, each at about a 90-degree angle from the two neighboring graspable components, as shown, e.g., in FIG. 1, FIGS. 6a, and 6c.

In some embodiments, the bucket features ergonomic design features. For example, in preferred embodiments, the gripping feature(s) on the bucket are configured for ease of use by a patient with, e.g., weak or small hands. For example, in some embodiments, the bucket comprises a plurality of gripping features on the exterior, distributed around the circumference of the bucket. In particularly preferred embodiments, the gripping features on the bucket are of sufficient depth and placement around the circumference of the bucket that the bucket may be approached from essentially any direction. In further preferred embodiments, the bucket may be securely gripped by holding gripping features that span less than one half the circumference of the bucket, preferably less than one third the circumference of the bucket. In certain embodiments, the bucket may be securely gripped using a single gripping feature on the exterior of the bucket.

In some embodiments, the container is configured for mixing the contents, e.g., a stool sample and buffer, without opening the container. In some embodiments, the bucket comprises at least one sample disruption feature on the inside surface, while in some embodiments, the bucket comprises a plurality of sample disruption features distributed on the inside surface.

In certain preferred embodiments, the sample disruption feature comprises a ridge and/or a bump.

In some embodiments, the sample disruption feature is fixedly attached to the inside surface of the bucket, and in certain preferred embodiments, the sample disruption feature is integrally formed on the inside surface of the bucket.

In some embodiments, the device is provided as a kit. In some embodiments, the kit comprises one or more of an instruction for use, and/or storage, shipping, or protective packaging configured to enclose the device.

In certain embodiments, the kit comprises a buffer solution, e.g., a buffer solution comprising a salt and a preservative or a stabilizing agent. In certain embodiments, the stabilizing agent may comprise a nucleic acid stabilizing agent In some embodiments, the kit may comprise other devices, e.g., a stool sampling device, and/or bracket for mounting the bucket on or under a seat of a toilet.

The invention herein provides a method for containing a stool sample, the method comprising, e.g., providing a device having a bucket, lid and seal as described above, depositing a stool specimen in the bucket, and engaging the lid and the bucket with the seal disposed therebetween, wherein the engaging comprises manipulating the bucket and the lid wherein a first engagement portion on the bucket is engaged with a mated engagement portion on the lid. In certain embodiments, a method further comprises adding a liquid, e.g., a buffer solution optionally comprising a salt and/or a preservative or a stabilizing agent, to the container prior to engaging the lid and the bucket to seal the container.

In some embodiments, the technology provides a method for homogenizing a stool sample within a sealed container as described above without re-opening the container prior to processing.

The technology further provides an enclosing holder for an ergonomic device as described above. In some embodiments an enclosing holder comprises a holder base comprising an interior cavity having a bottom surface and a top opening, and having a first engagement feature; a holder top comprising a mated engagement feature adapted to removeably engage with the first engagement feature of the enclosing base to form a leak-proof seal; a sample adapter; and a compression feature, wherein the sample adapter and the compression feature are configured to limit or prohibit motion of a sealed ergonomic device that is enclosed in the enclosing holder with respect to the enclosing holder, and wherein the enclosing holder is configured for use in a device for disrupting the sample in the enclosed ergonomic container, e.g. for use in a mechanical shaker (e.g., a powered device for mixing and/or emulsifying by agitation, including, e.g., a rotary shaker, a gyroscopic shaker, etc.). In certain embodiments, the cavity in the holder base has a depth from the bottom surface to the top opening that is greater than the height of an ergonomic device, e.g., a closed container in which the lid is firmly closed upon the bucket.

In some embodiments a sample adapter is configured to limit rotation of the ergonomic device enclosed in the enclosing holder around the central axis of the ergonomic device. For example, in some embodiments, the sample adapter is configured to fit or mate to a gripping feature on the exterior of the sealed ergonomic device when the device is enclosed in the holder. In certain preferred embodiments, the holder engages one or more gripping features on the bucket of the ergonomic device.

In some embodiments, the compression feature of the enclosing holder is configured to limit motion of the ergonomic device enclosed in the enclosing holder along the central axis of the ergonomic device. Compression features are not limited to any particular material or configuration and may be composed, e.g., of resilient material, such as compressible rubber or foam, or may comprise springs. In certain preferred embodiments, the compression feature comprises a compression spring, and in particularly preferred embodiments, the compression spring is disposed between the bottom surface of t holder base and the sample adapter.

The enclosing holder is not limited in its construction to particular materials. In preferred embodiments, the materials used to construct the enclosing holder are selected to withstand repeated sanitizing steps, e.g., washing, disinfecting, and/or sterilization, e.g., though use of steam or ultraviolet light. The materials of the holder may also be selected to withstand use in an homogenizing device, such as a mechanical shaker. In certain embodiments, the holder base and/or the holder top comprise or are composed of metal, and in particularly preferred embodiments, the holder base and/or the holder top comprise or are composed of steel, e.g., stainless steel.

The enclosing holder top is typically configured to engage the holder base in a secure manner. In certain embodiments, manipulation to engage a first engagement feature on the holder base with a mated engagement feature on the holder top comprises turning the holder top with respect to the holder base to effect the engagement.

The engagement features are not limited to any particular configuration, and may comprise, e.g., threaded feature, bayonet mount features, snap features, etc. In preferred embodiments, the first engagement feature and the mated engagement feature comprise flange features, e.g., that engage in the manner of a bayonet lens mount.

In certain embodiments, manipulation to engage the first engagement feature of the holder base with the mated engagement feature of the holder top comprises turning the holder top with respect to the holder base less than a full turn, e.g., a half turn (180 degrees), or a quarter turn (e.g., 90 degrees). In certain embodiments the manipulation comprises turning the holder top with respect to the holder base less no more than 45 degrees, and in certain embodiments, no more than 30 degrees.

In some embodiments, enclosing holder comprises a holder top assembly that comprises, e.g., the holder top and a gasket, wherein when the first engagement feature of the holder base is engaged with the mated engagement feature of the holder top, the gasket is disposed between the holder top and the holder base, e.g., to effect a seal at the junction between the base and the top. In certain embodiments, the holder top assembly comprises a gasket holder that holds the gasket, and the holder top in the holder top assembly is configured to travel partially or fully independently of the gasket holder during manipulation to engage the first engagement feature of the holder base with the mated engagement feature of the holder top. For example, if the holder top is engaged by rotating into position, the gasket holder may rotate only a portion of the way, or it may remain essentially stationary while the holder top rotates. In certain preferred embodiments, the gasket holder comprises a lid-engaging feature configured to engage a gripping feature a lid on an ergonomic device enclosed in the enclosing holder.

In some embodiments, the holder top assembly further comprises a handle, configured such that rotation of the handle rotates the holder top to engage the first engagement feature of the holder base with the mated engagement feature of the holder top, or to disengage the first engagement feature of the holder base from the mated engagement feature of the holder top. In some embodiments, the holder top assembly further comprising a reversible locking mechanism, wherein in a locked configuration, the locking mechanism prevents rotation of the handle to disengage the first engagement feature of the holder base with the mated engagement feature of the holder top.

The technology also provides methods of processing stool samples, comprising providing a sealed container, e.g., an ergonomic device, comprising a stool sample and a buffer, produced by the method described above; enclosing the sealed container in an enclosing holder such that the first engagement feature of the holder base is engaged with the mated engagement feature of the holder top; then shaking the enclosing holder in a mechanical shaker, such that the stool sample is dispersed in buffer within the sealed container.

The technology further contemplates compositions comprising a sealed container, e.g., an ergonomic device as described above, the composition comprising a stool sample produced by the method described above, wherein the sealed container comprising the stool sample is enclosed in an enclosing holder according the technology, wherein the first engagement feature of the holder base is engaged with the mated engagement feature of the holder top. The technology further contemplates a mechanical shaker containing the composition.

BRIEF DESCRIPTION OF THE DRAWINGS

These and other features, aspects, and advantages of the present technology will become better understood with regard to the following drawings:

FIG. 2A is a cross-sectional side view of an embodiment of a stool specimen container showing a lid (2), seal (3) with a vertical component (3b) and bucket (1).

FIG. 2B is a perspective top view of an embodiment of a floating plate seal (3) having raised features (3a) and a vertical component (3b).

FIG. 6, panel A and panel C show different embodiments of crossed gripping features (4a), combined with edge gripping features (4b). Panel B shows a handle gripping feature.

FIG. 15A shows drawings of different views of a lid (2); FIG. 15B shows drawings of different views of a floating plate seal (3); FIG. 15C shows drawings of a lid (2) and a floating plate seal (3), both separately and as an assembly with the seal inside the lid; and FIG. 15D shows drawings of different views of a bucket (1).

DEFINITIONS

Figure 1:
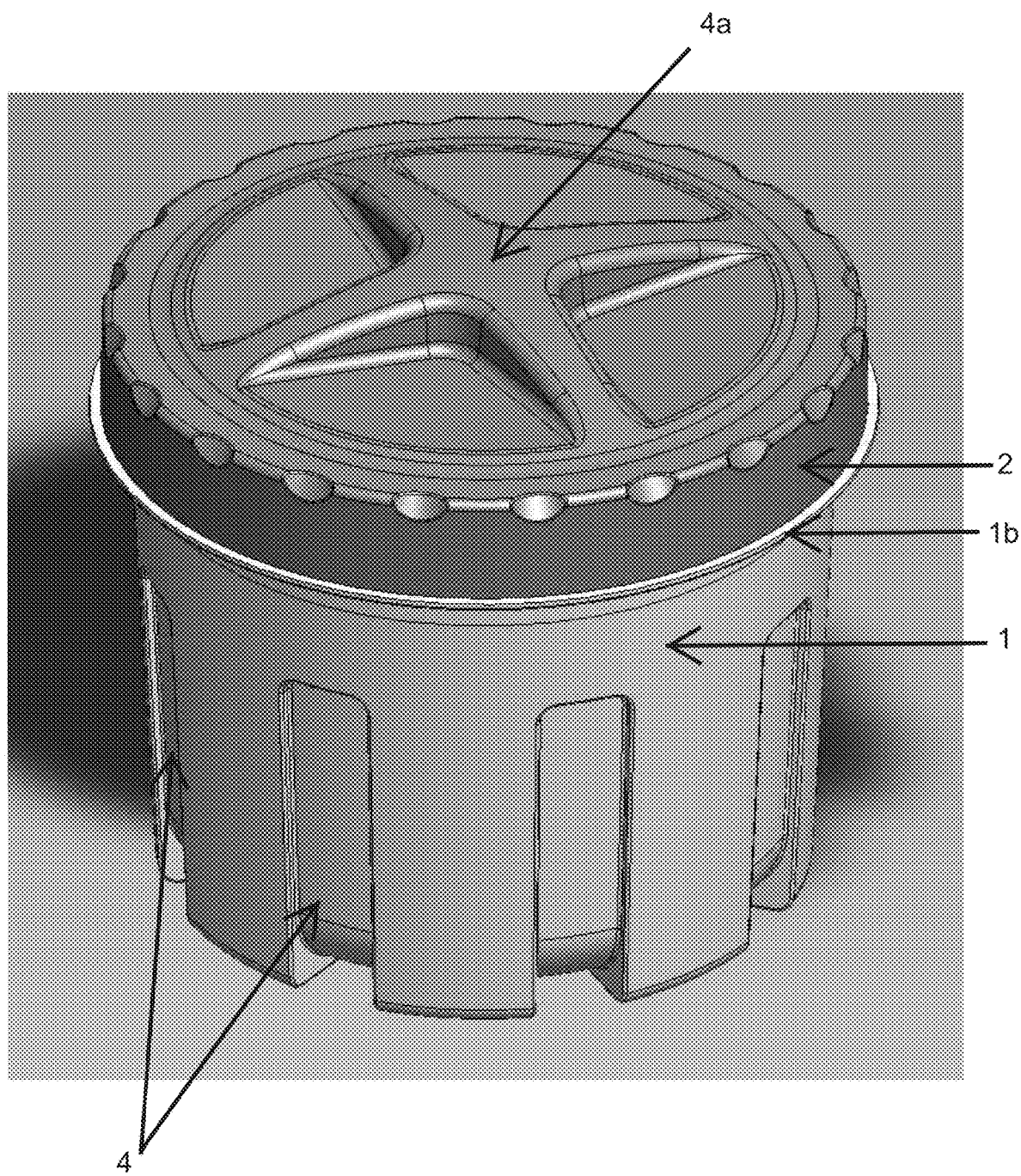
FIG. 1 is a drawing of an embodiment of a stool specimen container, a bucket (1) having a flange (1b), gripping features (4), and a lid (2) having a central crossed gripping feature and edge gripping features.
Figure 3:
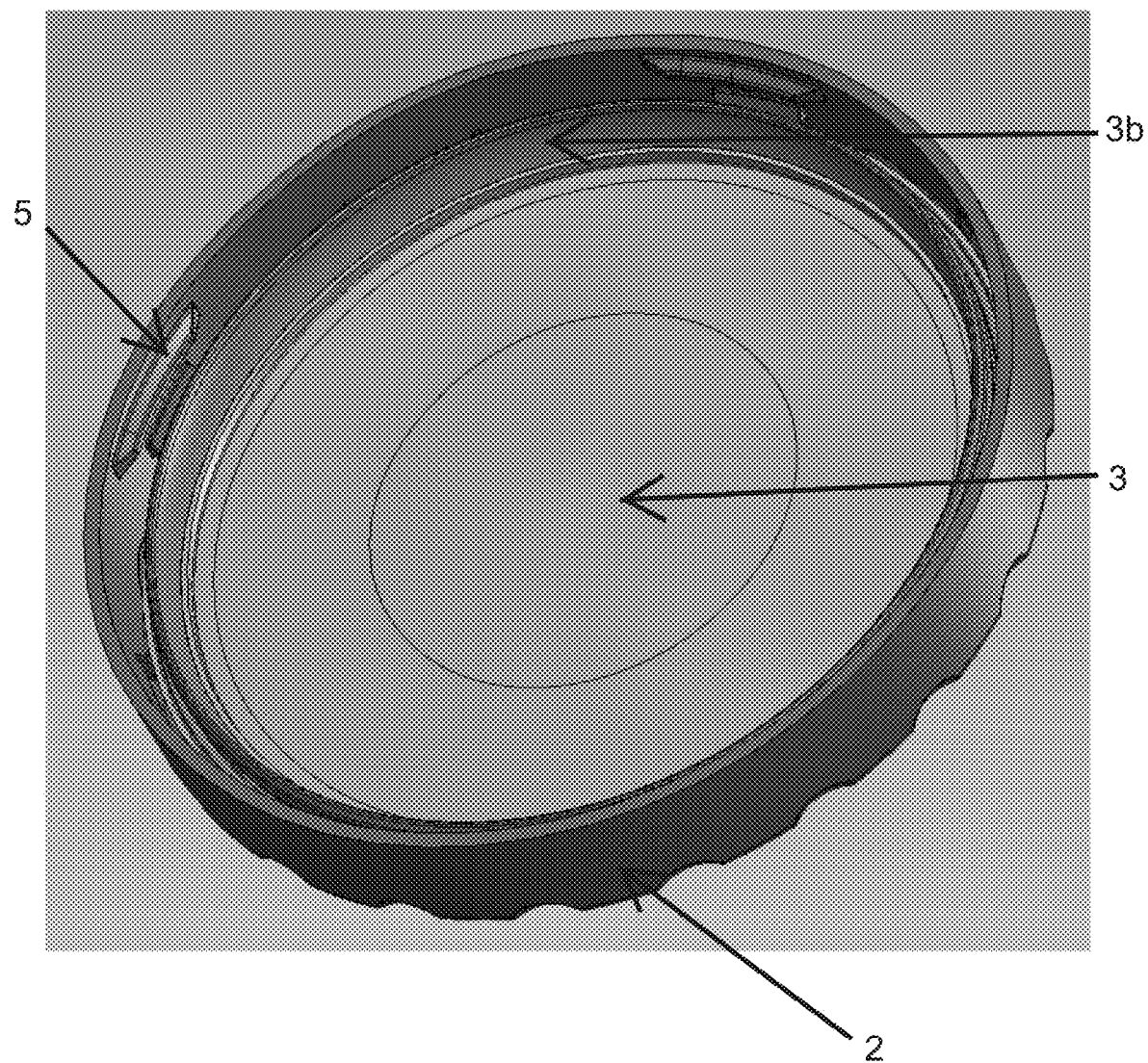
FIG. 3 is a drawing of an embodiment of a lid (2) and a floating plate seal (3) and an engagement portion (5).
Figure 4:
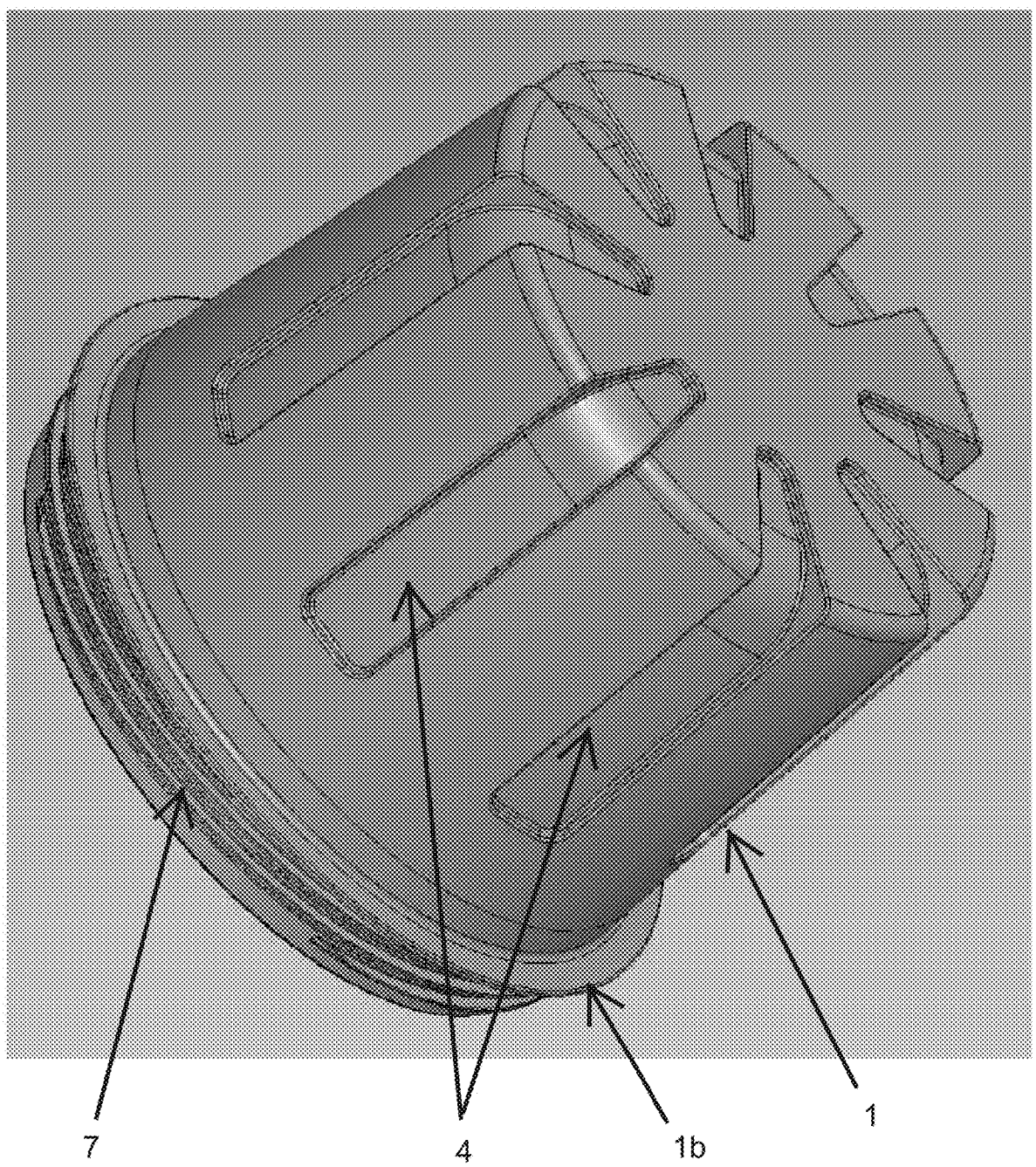
FIG. 4 is a perspective exterior view of an embodiment of a bucket (1) showing a flange (1b), gripping features (4), and an engagement portion that is a threaded portion (7).

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the term "analyte" is to be construed broadly as any compound, molecule, element, ion, or other substance of interest to be detected, identified, or characterized.

As used herein, the terms "subject" and "patient" refer to an animal, preferably a human, from which a stool specimen is collected. In some instances, the subject is also a "user" (and thus the user is also the subject or patient).

As used herein, the transitional phrase "consisting essentially of" as used in reference to compositions, steps, or other features is to be read as "consisting of" the specified materials, steps, or features, plus only unavoidable additional elements that do not materially affect the basic and novel characteristic(s) of the materials, methods, steps, etc., e.g., unavoidable contaminants, unavoidable steps.

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

As used herein, the term "kit" refers to any delivery system for delivering materials. In the context of sample collection systems, such delivery systems include systems that allow for the storage, transport, or delivery of devices or the samples collected therewith (e.g., buffers, stabilizers, preservatives, etc. in the appropriate containers) and/or supporting materials (e.g., written instructions for performing a procedure, etc.) from one location to another. For example, kits include one or more enclosures (e.g., boxes) containing the relevant devices and supporting materials. As used herein, the term "fragmented kit" refers to a delivery system comprising two or more separate containers that each contains a subportion of the total kit components. The containers may be delivered to the intended recipient together or separately. For example, a first container may contain materials for sample collection and a buffer, while a second container contains sampling devices, separate shipping materials, etc. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website, a remote server of a service provider, etc.

The term "ergonomic" as used herein in reference to designs or features, e.g., of an article or system, refers to designs or features optimized for use by the intended human user, e.g., to avoid unnecessary stress, fatigue, or unintended improper use, or to accommodate special needs of a human user. For example, a device having ergonomic features optimized for geriatric users may have features especially designed or selected to accommodate conditions and/or disabilities common in a population of geriatric persons, e.g., arthritis, muscle weakness, carpal tunnel syndrome, epicondylitis, vision impairment, etc.

As used herein, the term "central axis," as used in reference to a container or ergonomic device, refers to an axis about which the container device has rotational symmetry. For example, in ergonomic devices depicted in FIGS. 1, 6A-6C, 7-10 and 15A-15D, the central axis is defined by the line between the point at the center of the bottom of the bucket and the point at the center of the lid, when the lid is engaged with the bucket.

The term "geriatric" as used in reference to a subject or patient or a user of a device, refers to an aged or elderly person, e.g., a person over about 65 years of age. There is no defined age for "geriatric" thus in some instances it may be e.g. a person over about 50 years of age.

DETAILED DESCRIPTION OF THE INVENTION

Embodiments of the invention are described in this Detailed Description of the Invention, and in the Summary above, which is incorporated here by reference. Although the invention has been described in connection with specific embodiments, it should be understood that the invention as claimed should not be unduly limited to such specific embodiments. Those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter of the technology. Accordingly, all such modifications are intended to be included within the scope of the present invention as defined in the appended claims.

Provided herein is technology relating to collecting samples and particularly, but not exclusively, to technology for collecting, a stool specimen. As discussed above, a particular challenge when subjects or patients collect stool samples, e.g., in the home, is the need for a collection container that is 1) sufficiently easy to manipulate that the container can be reliably and securely closed and sealed by subjects who may have conditions and/or disabilities that make manipulating containers difficult, e.g., arthritis, muscle weakness, carpal tunnel syndrome, epicondylitis, vision impairment, etc., but that, when closed, is sealed with a sufficiently reliable seal that there is little or no chance of leakage during transport and/or downstream processing, e.g., shaking homogenization.

Provided herein is technology for acquisition of a stool specimen by a subject providing the stool specimen, the technology having features directed to ensuring proper sealing, even when used by subjects having disabilities such as are discussed above, such that leakage during handling, shipping, and processing is minimized or eliminated. The technology thus contemplates a sample collection container having ergonomic features, such that it can be manipulated by a subject, e.g., a geriatric patient, into a securely closed and leak-proof configuration.

The technology is further directed to improved safety and efficiency in processing collected specimens, e.g., in a clinical or research lab. The technology thus provides systems and methods for processing a stool sample, e.g., by dispersing or homogenizing the stool in buffer, directly in the container in which it has been collected by a subject, without the need to transfer the sample to a different container, or even to open the collection container received from the subject. The technology provides an enclosing holder to support and contain a sealed sample collection container, e.g., during mechanical shaking.

The technology includes and contemplates devices and related embodiments such as those embodiments portrayed in FIGS. 1-14. In these embodiments, a specimen container comprises a 3-piece design comprising a bucket (1), a lid (2), and a seal (3), in which the bucket and lid are configured with mated engagement features to securely engage the lid to the bucket with the seal disposed therebetween to seal sample contents, e.g., a stool sample, a liquid buffer, etc., within the container in a leak-proof manner when the engagement features are engaged. In certain preferred embodiments, the seal has a floating design, e.g., it may be a floating plate as diagrammed in FIGS. 2A and 2B or 14A, such that the lid and the bucket travel independently of the seal, e.g., during rotation of the lid with respect to the bucket to engage the lid with the bucket, thereby reducing the force necessary to tightly close the container. Although the seal in certain embodiments is configured to travel independently of the lid during closing (or opening) of the container, in some embodiments the floating seal and lid are configured together as a lid assembly e.g., wherein the floating seal is retained in the lid, e.g. by a ridge, bump or other retaining feature that permits the seal to float within the lid.

In certain embodiments the combination of lid and seal comprises features to reduce friction between the lid and seal. For example, in some embodiments, a lid and/or a floating seal comprise one or more raised features disposed between the lid and the seal/floating plate, features that minimize the amount of contact between these components and thereby minimize friction between these components during manipulation to close or open the container. In some embodiments the raised features are on the lid itself, while in other embodiments, the raised feature(s) are on the seal, e.g., on the side of a floating plate disposed toward the lid. In some embodiments, both the lid and the floating seal comprise one or more raised features.

The embodiments are not limited to any particular configuration of raised features. For example, FIG. 2B shows one example of a raised feature (3a) comprising a radial design, while FIG. 14A shows another configuration, comprising dispersed bumps on a top surface of a floating plate. FIGS. 14B-14D show the raised features (3a) between the lid (2) and the seal (3).

In some embodiments, a raised feature may also serve other functions. For example, a raised feature may serve to change the shape of the seal and/or lid upon engagement of the lid to the bucket. For example, the raised feature (3a) shown in FIG. 2 may be configured to flex the seal (3) upon engagement of the lid to the bucket, e.g., to form the seal plate into a cupped shape, thereby enhancing performance of the seal in certain design configurations. For example, flexing the seal may enhance contact between a vertical component of a floating plate seal and a vertical surface of the bucket.

Figure 11:
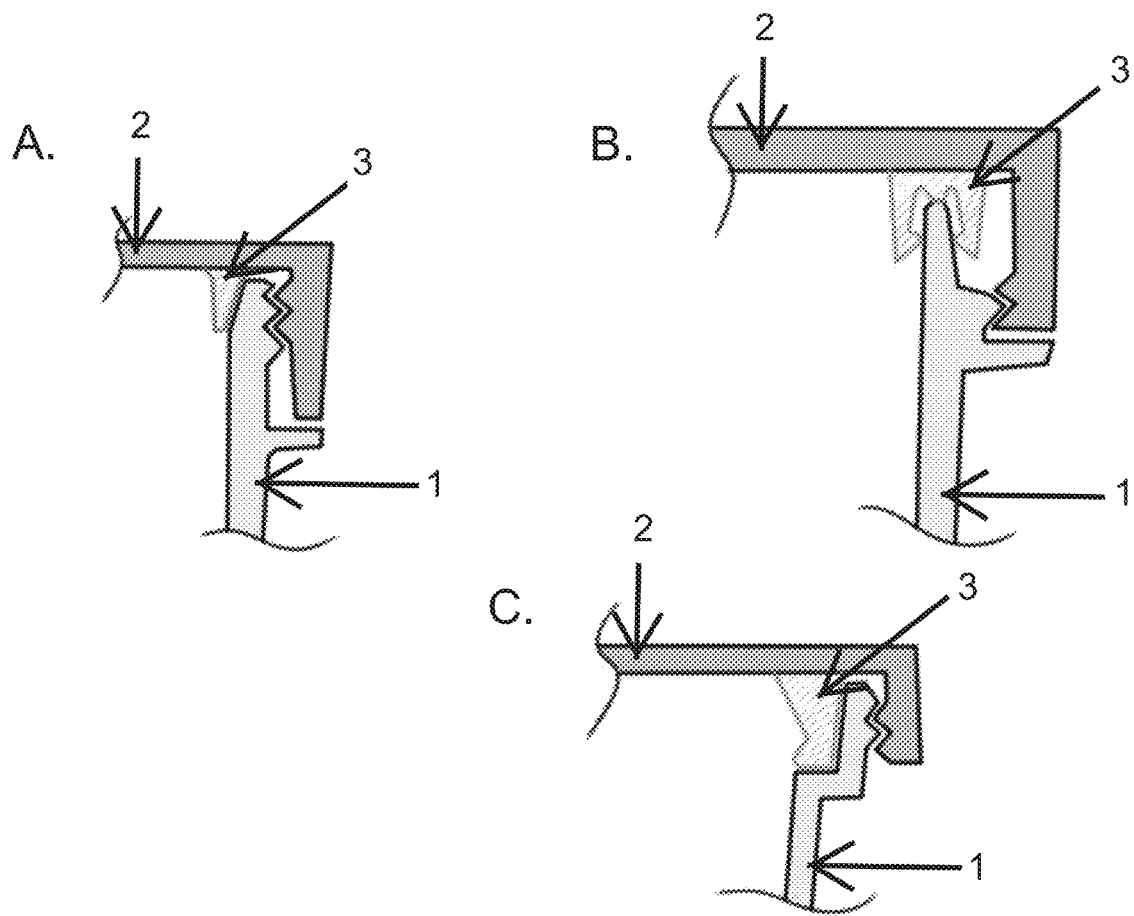
FIG. 11, panels A-C is a cross sectional view of different embodiments of seals (3) between lids (2) and the top edge and/or side of a bucket (1).
Figure 12:
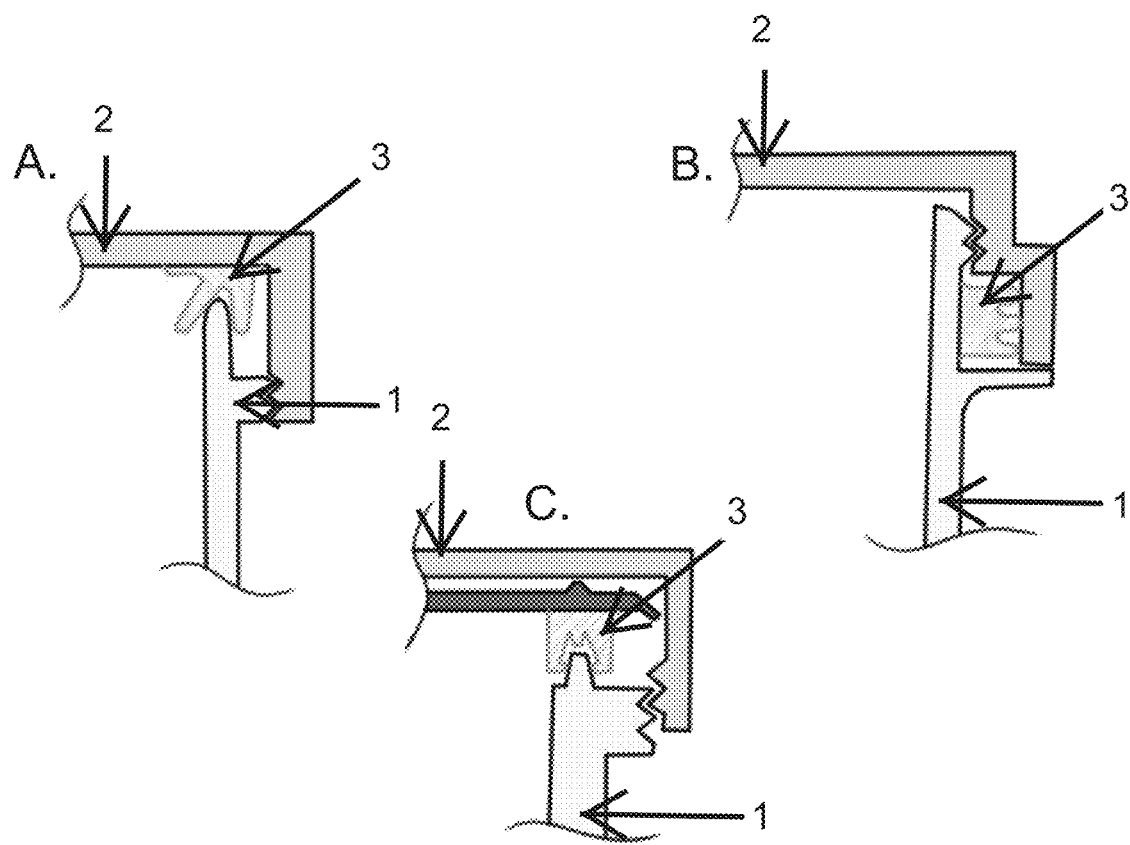
FIG. 12, panels A-C, is a cross sectional view of different embodiments of seals (3) between lids (2) and the top edge and/or side of a bucket (1).
Figure 13:
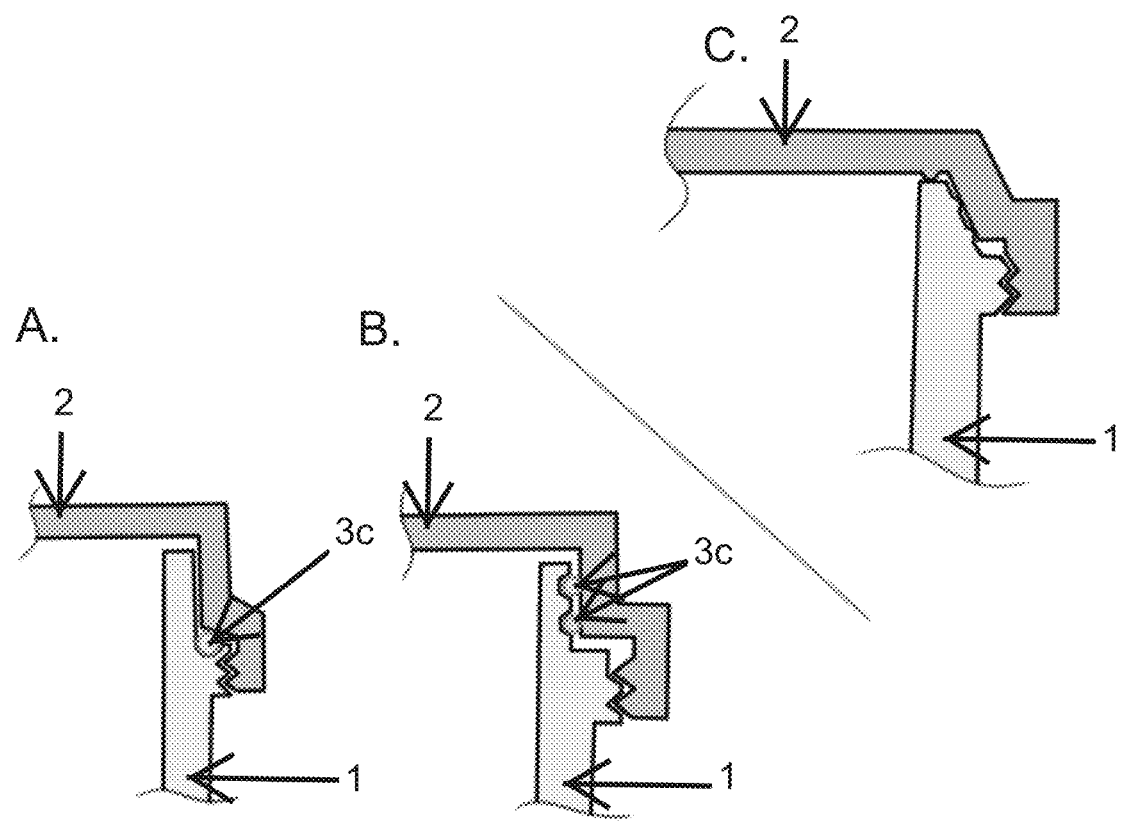
FIG. 13, panels A-C, is a cross sectional view of different embodiments of seals (3) between lids (2) and the top edge and/or side of a bucket (1).
Figure 14:
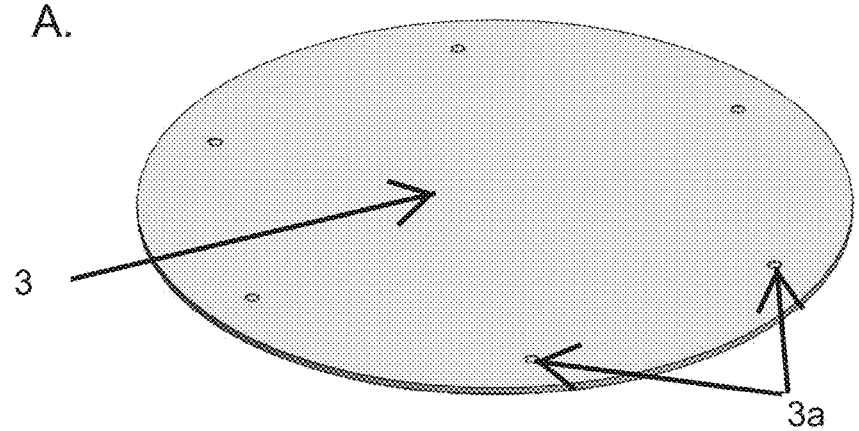
FIG. 14, panels A-D. Panel A is a drawing of an embodiment of a floating plate seal (3) showing raised features (3a) on the top surface. Panels B-D show cross sectional views of embodiments of a floating plate seal (3) in place in a lid (2) engaged to a bucket (1), showing a raised feature (3a) on the top surface of floating plate seal (3) contacting lid (2), and vertical component (3b) of the floating plate seal (3) forming a seal with the interior surface of bucket (1). Compressible components (3c) are indicated.
Figure 14:
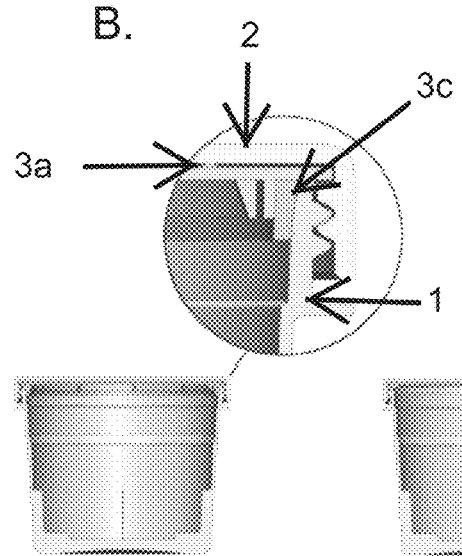
Figure 14:
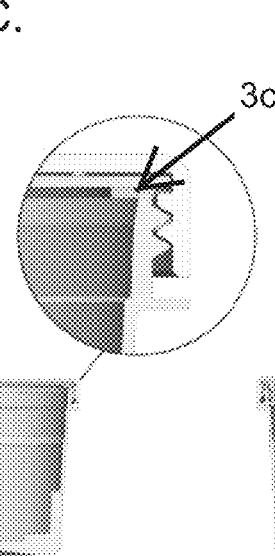
Figure 14:
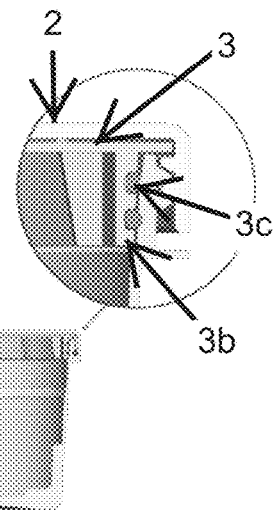

Seal configurations are not limited to any particular design and a number of different sealing options are possible. In some embodiments, one or more of the components of the device comprises a compressible component that is compressed when the lid is engaged with the bucket. For example, in some embodiments, the seal, e.g., a floating plate seal, includes a compressible seating surface that is compressed between the floating plate and a portion of the bucket (e.g., the top edge of the bucket) when the lid is engaged with the bucket. In certain preferred embodiments, the seal combines a flat or cupped horizontal surface perpendicular to the bucket wall and a vertical component configured to form a seal with and against the inside of the bucket wall. See, e.g., the cross-section of the assembly shown in FIG. 2A. Numerous additional sealing configurations are shown in FIGS. 11-13. The device is not limited in the shape of the components, provided they fit together and operate as described.

In some embodiments, an ergonomic device according to the invention comprises features to reduce the likelihood of incorrect use by a user, e.g., incorrect alignment of the lid and bucket during closure by a user, causing, for example torn or pinched gasket, improper seating, leakage, etc. In some embodiments, for example, the lid and/or ergonomic bucket of the container comprise features that assist a user in establishing correct alignment between the lid and bucket during the process of engaging the lid to the bucket.

Figure 16:
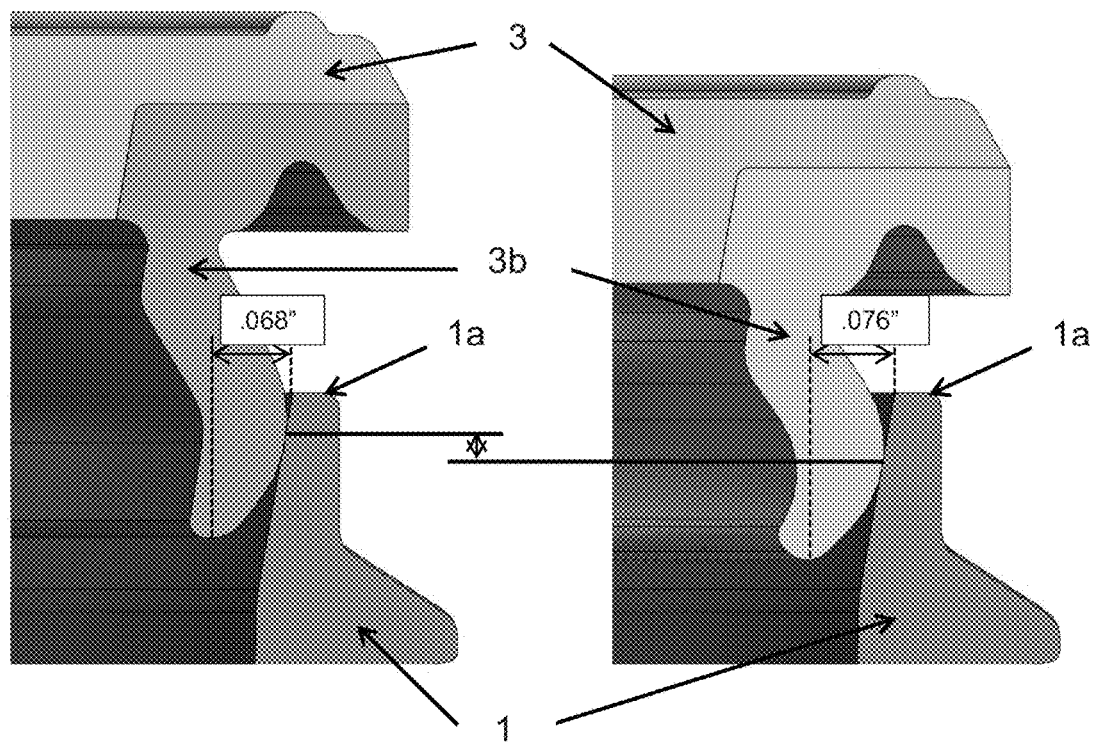
FIG. 16, panels A-E, show cross sectional views of different embodiments of vertical component (3b) of floating plate seal (3) as they contact the top edge and/or side of bucket (1).
Figure 16:
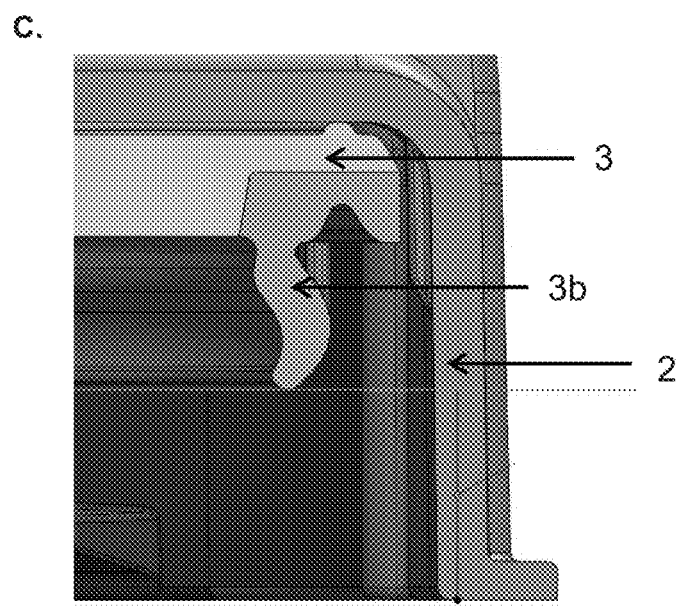
Figure 16:
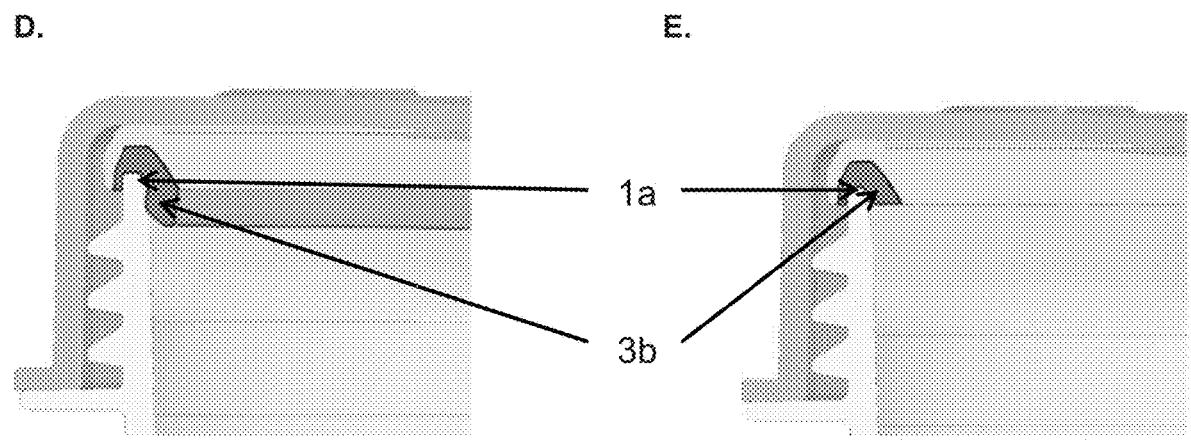

In some embodiments, for example, the vertical component 3(b) of the seal (3) may be modified to promote proper alignment and/or to prevent pinching or tearing of the seal. For example, the seal may be configured to curve away from the interior sidewall of the bucket as shown (e.g., as diagrammed in FIG. 16A-16C) to provide a gap to lead the top edge of the bucket into the correct position between the vertical component (3b) of the seal (3). Such an inward curve at the lower edge of the vertical component also reduces the risk of catching the edge of vertical component (3b) on the top surface (1a) at the rim of the bucket. In some embodiments, the vertical component 3(b) may be shortened, e.g., as shown in FIG. 16B, and/or a stiffer seal material may be selected to reduce the probability of the lip of the bucket catching on and damaging the seal. In some embodiments, a seal may be configured to have a short vertical component (3b), as exemplified in FIGS. 16D and 16E. In certain embodiments, the seal cups the top surface (1a) of the rim of bucket (1), e.g., as shown in FIG. 16E.

Figure 17:
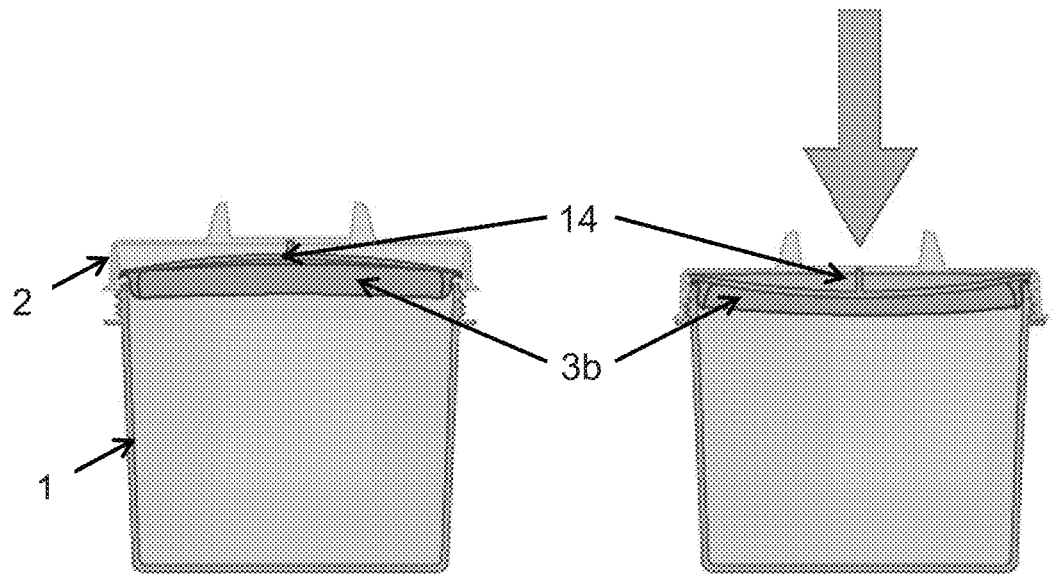
FIG. 17, panels A-B. Panel A shows an embodiment comprising a pop-over plate (14), configured to expand seal (3) when lid (2) is engaged with bucket (1). Panel B shows an embodiment wherein the seal (3) is an expandable seal, configured to expand outward when lid (2) is engaged with bucket (1).
Figure 17:
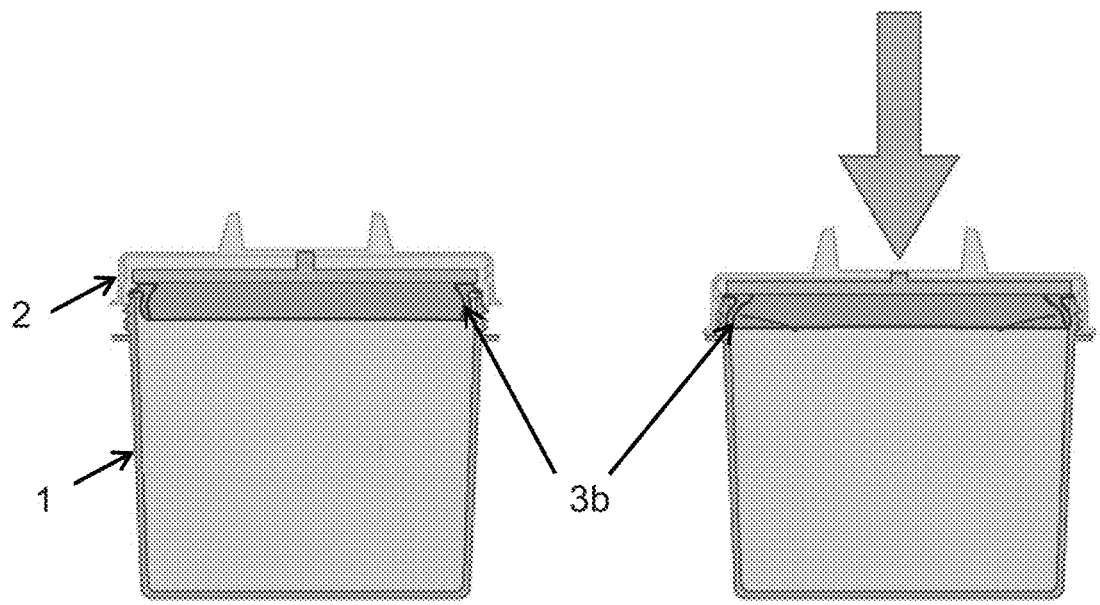
Figure 18:
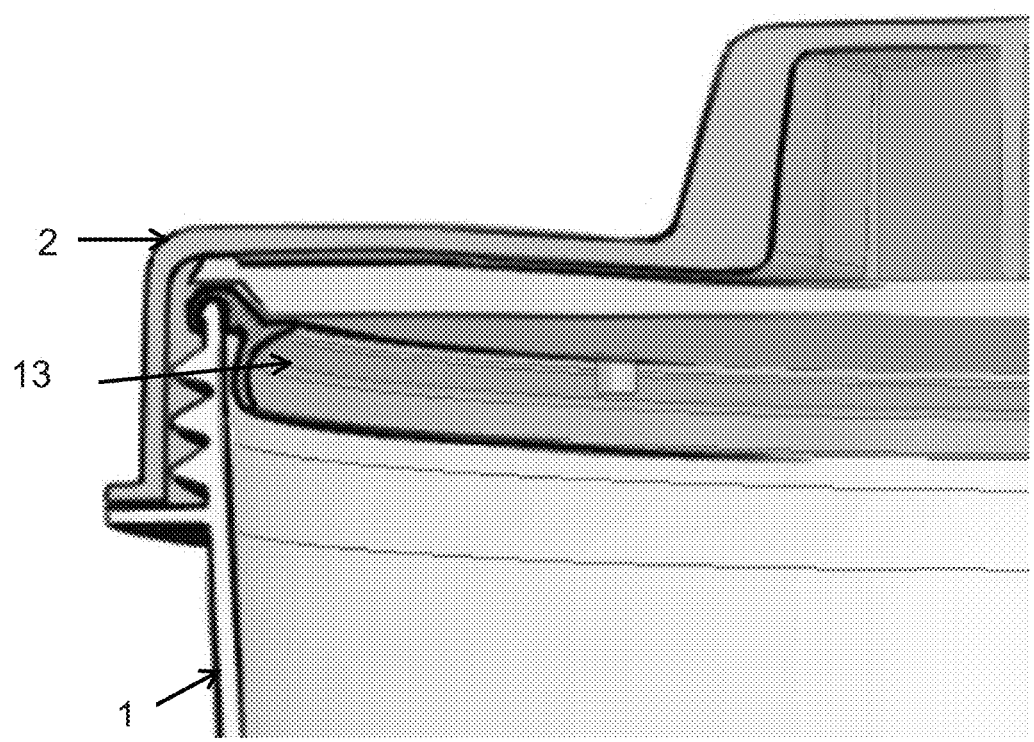
FIG. 18 is a cross-sectional view of a separate gasket (13).

In some embodiments, a container may comprise a feature that repositions vertical component (3b) of seal (3) to contact the circumferential vertical surface of bucket (1) only after lid (2) is properly seated on bucket (1). For example, FIG. 17A shows a lid (2) comprising a seal having a vertical component (3b) that is in a first position curving away from the circumferential vertical surface on the interior of bucket (1), providing a better approach for inserting the rim of bucket (1). A pop-over plate (14) having a lens-like geometry is configured flex when lid (2) is properly engaged to bucket (1), thereby moving vertical component (3b) of the seal into a second, sealing position. In the embodiment shown in FIG. 17A, pressure of lid (2) and/or bucket (1) on pop-over plate (14) upon engagement of lid (2) to bucket (1) causes the pop-over plate to flex in a manner that moves vertical component (3b) radially outwards and into contact with the circumferential vertical surface of bucket (1). The same effect may be achieved using a number of different sealing configurations. For example, as diagrammed in FIG. 17B, in some embodiments seal (3) itself is an expanding seal that is configured to flex upon engagement of lid (2) to bucket (1), such that pressures of lid (2) and/or the bucket (1) on the seal cause vertical component (3b) of the seal to flex radially outward toward the circumferential vertical surface of bucket (1) when the lid is properly engaged to the bucket. In other embodiments, a separate gasket (13) that is not part of a lid may be provided, e.g., on the top edge of the bucket, such that a seal is formed when the lid is engaged with the bucket, as shown in FIG. 18.

Figure 19:
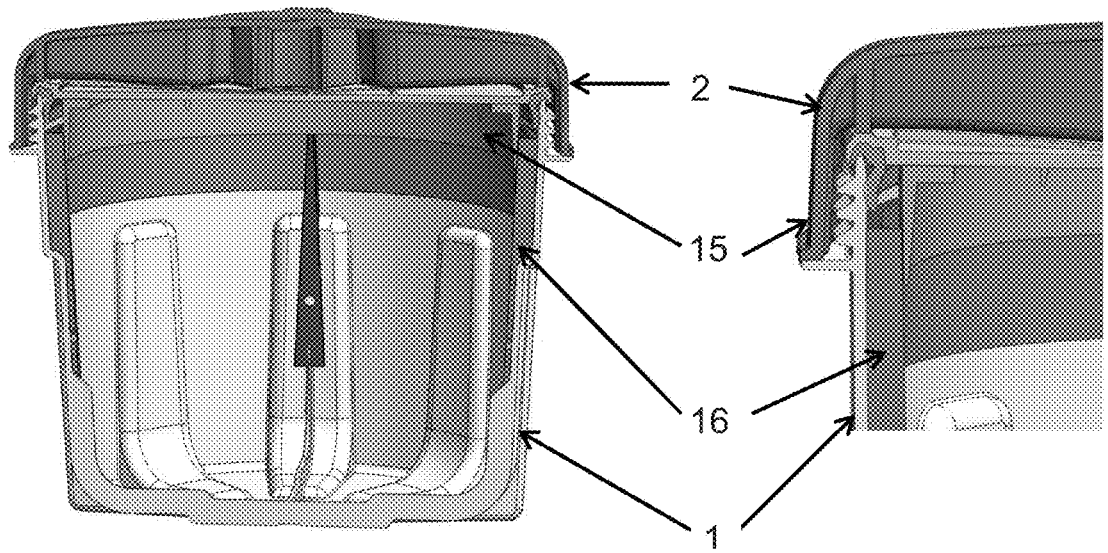
FIG. 19, panels A-D. Panels A-B show cross-sectional views of an embodiment of an alignment ring (15) and a bucket comprising guide ribs (16). Panels C-D show cross-sectional views of an embodiment of an a support ring (17).
Figure 19:
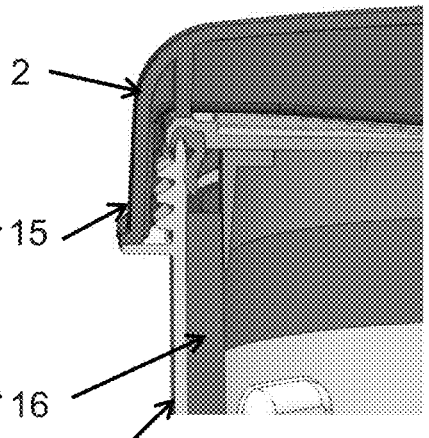
Figure 19:
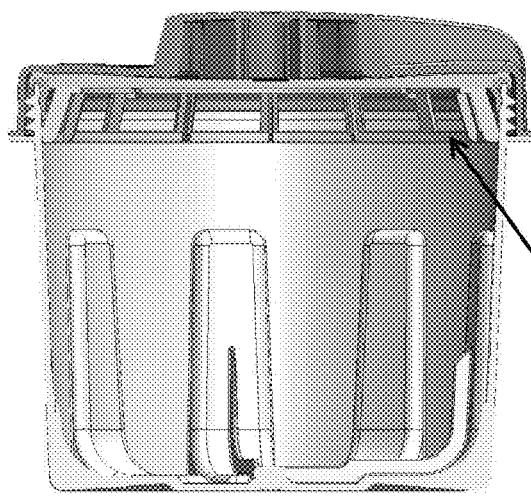
Figure 19:
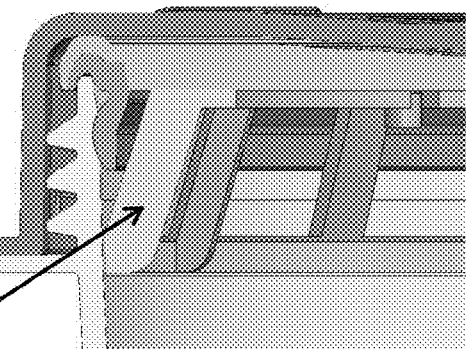

In some embodiments, both the lid (2) and bucket (1) may comprise components that guide the bucket and lid into proper alignment during the container closing process. For example, in some embodiments, lid (2) comprises an alignment ring (15) that positions the top edge of bucket (1) at it approaches the seal during the closing process as shown in FIGS. 19A and 19B. In some embodiments, bucket (1) may comprise guide ribs (16) that interact with an alignment ring to properly position the lid and bucket for engagement, as shown in FIGS. 19A and 19B. In other embodiments, lid (2) may comprise an internal support ring (17), e.g., as shown in FIGS. 19B and 19C, configured to assure that the mated engagement portions of the lid and bucket are properly aligned when they contact for engagement.

Figure 20:
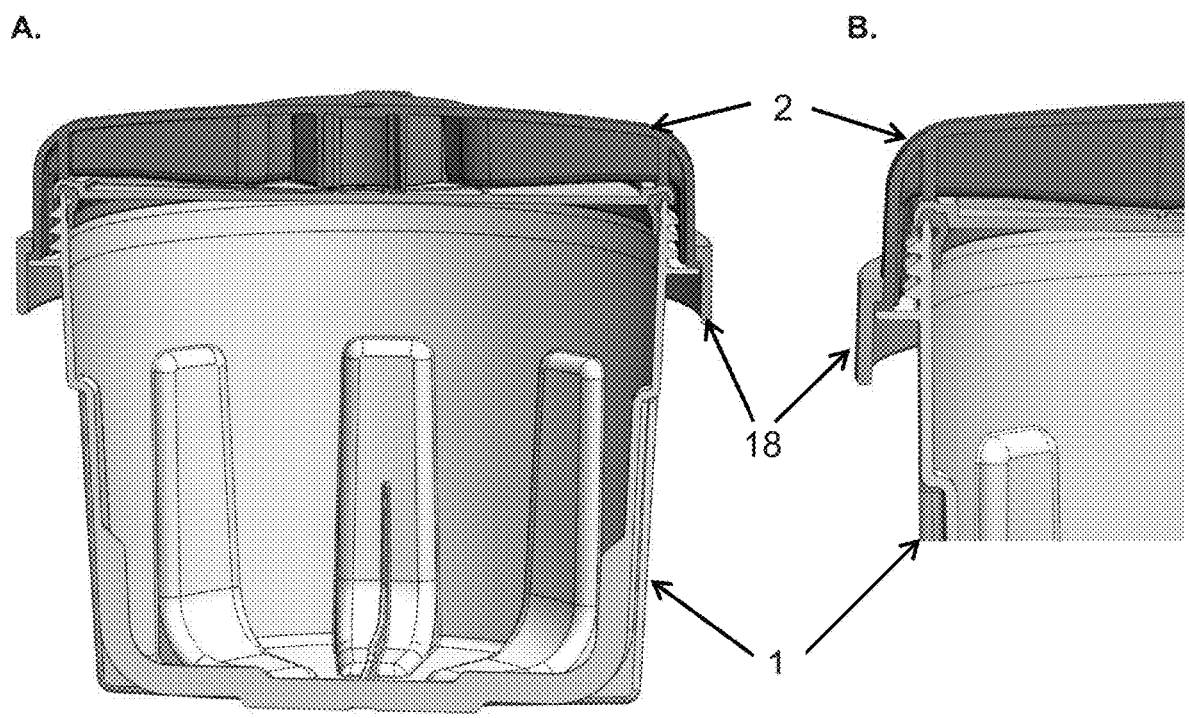
FIG. 20, panels A-B, show cross-sectional views of an embodiment of a skirt (18) on lid (2).

In yet other embodiments, the lid (2) may comprise an external feature that restricts the angle at which the top edge of the bucket can be brought into contact with the seal within the lid. For example, an external skirt (18) feature, as shown in FIGS. 20A and 20B. may be provided. In preferred embodiments, the external skirt is sufficiently long and of sufficient rigidity that the mated engagement portions of the lid and bucket cannot be brought into contact unless and until the lid and bucket are in sufficiently proper alignment to prevent crimping, tearing, or other damage to a seal or gasket during engagement of the lid to the bucket, and to ensure proper engagement of the mated engagement portions. The skilled person can readily determine by measurement and/or testing a length and diameter of an external skirt suitable for providing proper alignment between lids and buckets of containers having a wide array of different dimensions. In some embodiments, an external skirt (18) on lid (2) is manufactured as an integral part of the body of lid (2), while in other embodiments, an external skirt (18) is a separate component part that is reversibly or irreversibly affixed to lid (2).

Figure 21:
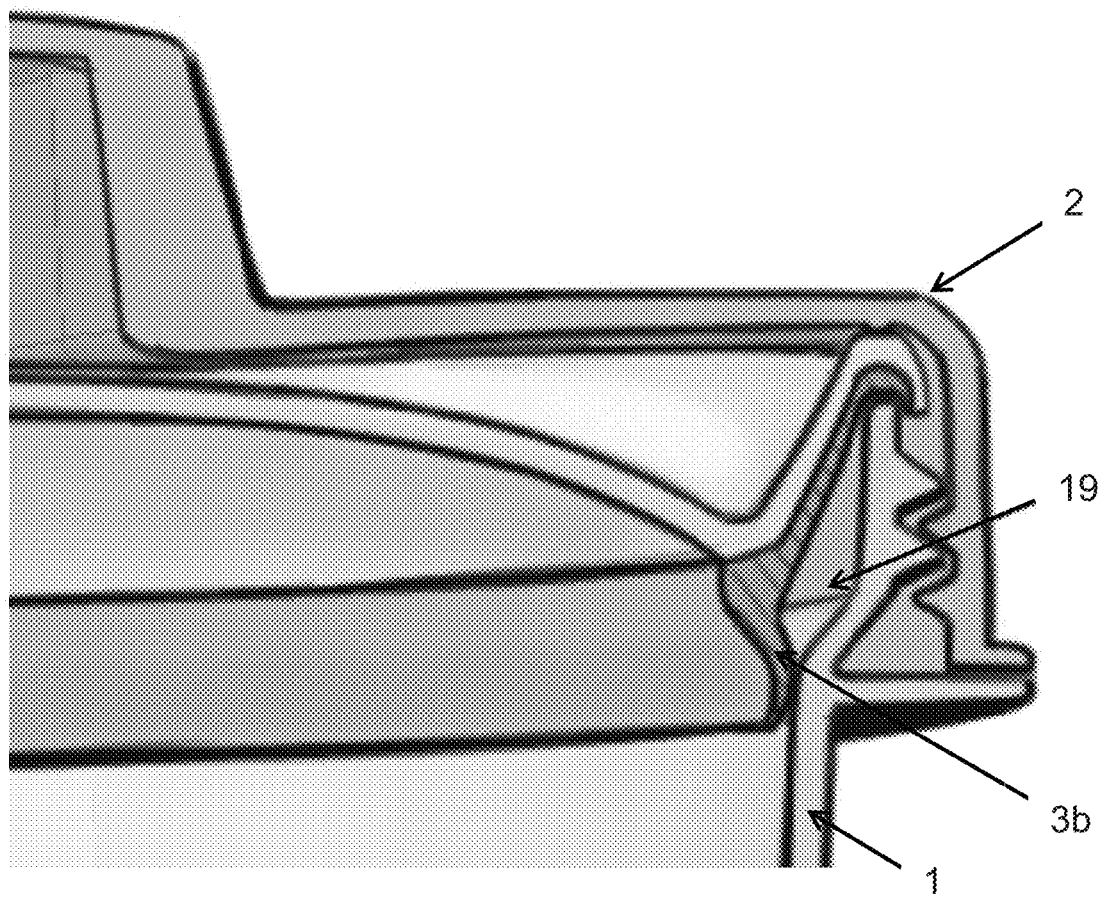
FIG. 21 is a cross-sectional detail view of a portion of a bucket (1), showing a funnel portion (19) on bucket (1).

In yet other embodiments, bucket (1) may comprise a funnel portion (19) that provides a wider opening for the approach of the vertical component (3b) of seal (3) into the bucket opening, and gets progressively narrower, such that the seal (3) contacts the circumferential vertical surface of bucket (1) below the funnel portion (19) of bucket (1), e.g., as diagrammed in FIG. 21.

The guiding features discussed above are not limited to any particular construction. For example, alignment rings, guide ribs, support rings, skirts, etc. may be made of the same material as the lid and/or bucket, or of different material. In some embodiments, for example, these features are manufactured as integral parts of the component on which they appear and in some embodiments, they are provided as separate parts that are reversibly or irreversibly attached to the component on which they are used. In certain embodiments, the ergonomic bucket of the container comprises gripping features designed to facilitate grasping of the bucket by an adult person with limited hand size and/or strength, e.g., a geriatric patient. For example, the bucket may comprise gripping ridges configured to permit an adult to grasp the ridges with several fingers of one hand, i.e., ridges of sufficient height (top to bottom with respect to the top and bottom of the bucket), e.g., to admit 2 to 3 fingertips to contact a side of a ridge when, for example, the thumb is in contact with another side of the same or a different ridge to provide an opposing gripping force.

The plurality of gripping ridges define grooves on the surface of the bucket by their spacing, i.e., the space between each pair of adjacent ridges may be considered as a groove. In preferred embodiments, grooves are of sufficient depth to permit fingertips to find purchase on the sides of the ridges. Grooves are not limited to a particular depth but may be, for example, about 0.2" to 1" or more in depth, or any fraction thereof (e.g., 0.25", 0.3", 0.4" . . . 0.9", 0.95", etc.). In preferred embodiments, a plurality of ridges are distributed circumferentially around the bucket. It is contemplated that suitable ergonomic gripping features may comprise grooves, ridges, bumps, dips, or any other surface convexities and concavities, or combinations thereof.

In some embodiments, a container according to the invention includes features configured to facilitate mixing the contents within the sealed container without opening the container, e.g., through agitation of the sealed container (by, e.g., shaking, rotating, vibrating, etc.). In some embodiments, the bucket/and or the lid assembly of the container comprise one or more internal sample disruption features, e.g., interior ridges, bumps, or other features that intrude into the interior space within the closed container. In preferred embodiments, sample disruption feature(s) are fixedly attached to the container when sealed i.e., the sample disruption feature(s) do not move significantly with respect to the sealed container (do not rotate or spin, for example) during agitation of the container. In particularly preferred embodiments, the sample disruption feature(s) are integrally formed on the interior of the bucket and/or lid.

The container is preferably constructed of unbreakable material. For example, in preferred embodiments, the container comprises or is composed of plastic and/or rubber. Suitable materials may be natural or synthetic, and include but are not limited to, e.g., polypropylene, polyethylene, polycarbonate, polystyrene, polyvinylchloride, polyamides, etc. Plant-based and/or biodegradable plastics are also contemplated for use. In preferred embodiments, the one or more parts of the device are at least partially, preferably completely opaque. The bucket, lid and seal may be composed of the same materials or different materials. In preferred embodiments, the materials are recyclable after stool samples are collected and processed.

The devices provided are associated with related methods. For example, a method for obtaining a stool specimen includes the steps of providing the device, depositing a specimen in the bucket of the device, and sealing the device by engaging the lid to the bucket using the engagement features, and sending or delivering the container and specimen for analysis, e.g., to a physician's office or testing lab.

Figure 22A:
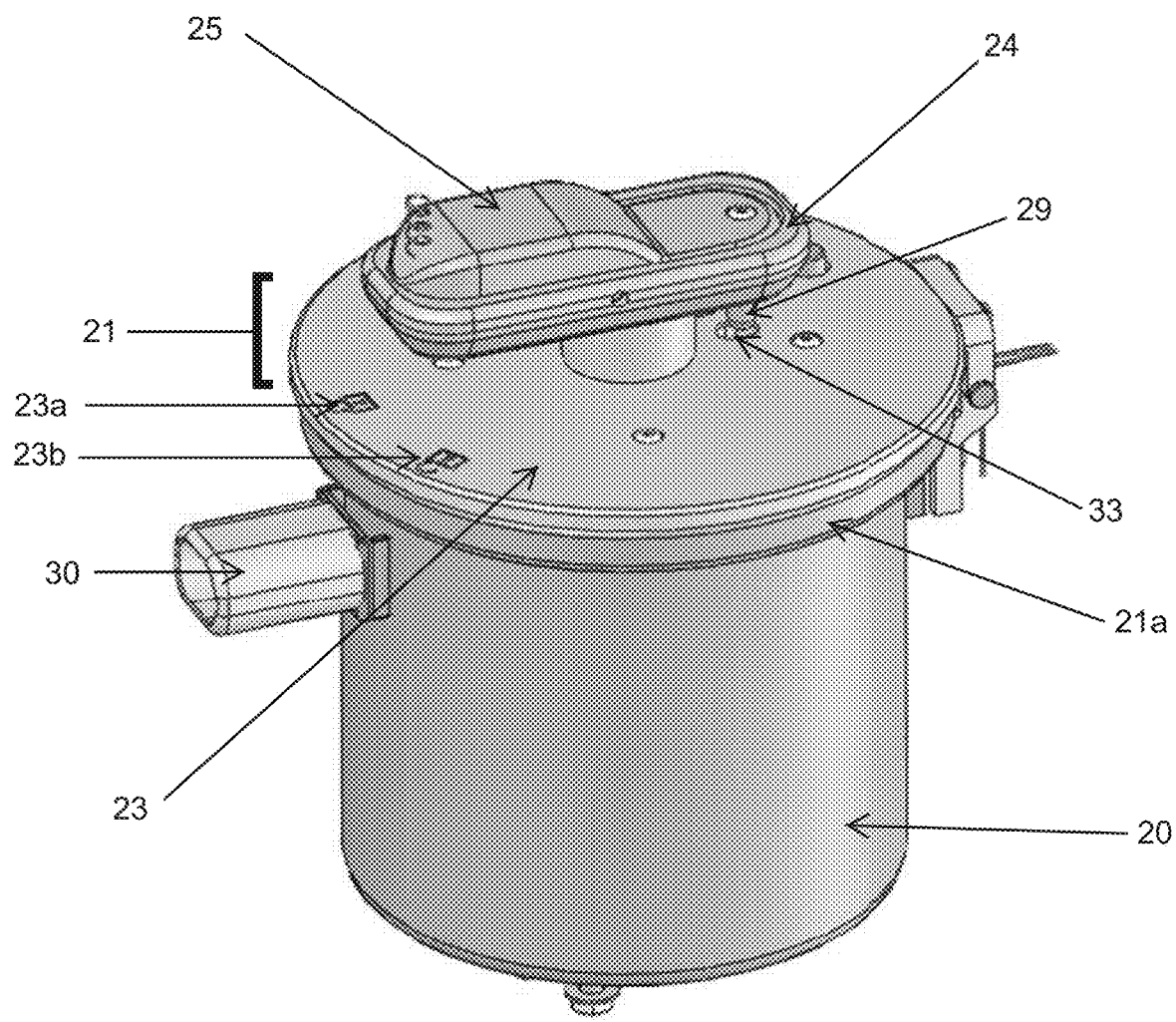
FIGS. 22A-22E show views of an embodiment of an enclosing holder for an ergonomic stool specimen container as shown in FIGS. 15A-15D.
Figure 22B:
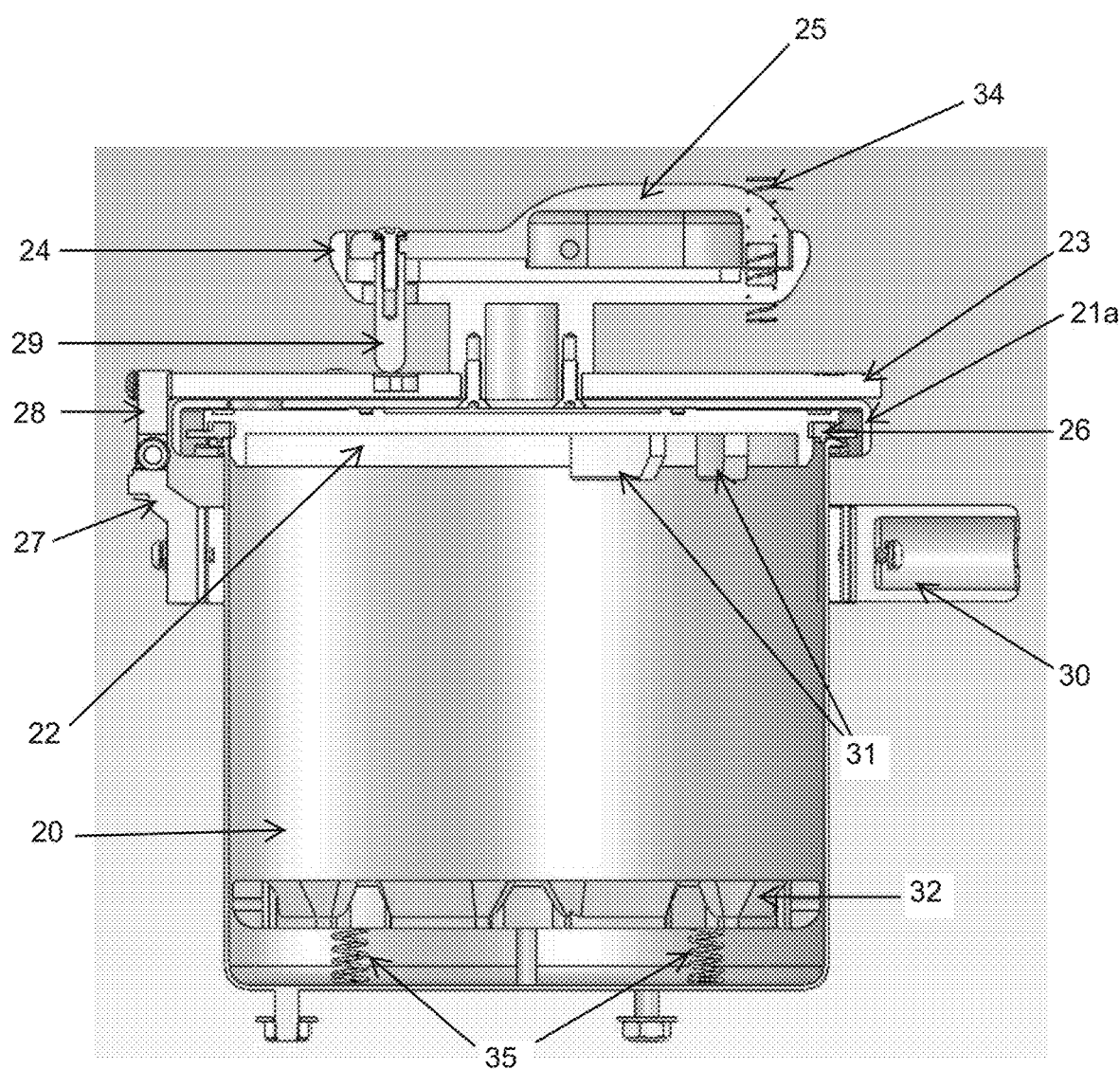

In some embodiments, the invention provides an enclosing holder adapted to receive and enclose an ergonomic container according to the invention, e.g., during processing for mixing the contents within the sealed container, e.g., through agitation of the sealed container (by, for example, shaking, rotating, vibrating, gyroscopic mixing, etc.). In some embodiments, the enclosing holder is configured to securely seal, such that any contents leaking from an ergonomic stool collection container, e.g., during vigorous agitation, are completely contained within the enclosing holder, thereby reducing risk of accidental worker exposure to leaked biological samples. In preferred embodiments, an enclosing holder is configured with internal features that mate to external features on the ergonomic sample container, such that a sample container is securely held within the enclosing holder when the enclosing holder is secured in a closed state. For example, FIG. 22B shows a cross-sectional view of an embodiment of an enclosing holder comprising a sample adaptor (32) that comprises ridges configured to mate with gripping features (4) on the exterior of the container shown in FIG. 1, such that when the container is fitted within the sample adaptor (32) and the enclosing holder is closed, rotational movement of the bucket within the enclosing holder is restricted or, preferably, prevented.

In some embodiments, an enclosing holder comprises a holder top assembly (21) attached to holder base (20), e.g., via a hinge. As shown in an exemplary embodiment in FIG. 22B, a hinge may comprise a hinge body (27) attached to the holder base (20), with or without a spacer, and a hinge top (28) attached to the holder top assembly (21).

In some embodiments, a holder top assembly (21) comprises a handle configured to actuate engagement of the top assembly (21) to the base (20) of the enclosing holder. For example, in some embodiments, when the holder top assembly is positioned on the top of the holder base in preparation for engaging, rotation of a handle actuates engagement of mated engagement features on the holder top assembly and the holder base. For example, in some embodiments, the holder top assembly (21) and holder base (20) comprise mated engagement features, such as mated flange features (21b, 20a), e.g., as shown in FIG. 22D, which are engaged by placing the holder top assembly on the holder base and twisting the handle so as to lock the holder top assembly to the holder base in a manner similar to a bayonet-style lens mount. In preferred embodiments, the holder top assembly (21) and/or the holder base comprise a gasket (26) to seal the enclosing holder when the lid assembly (21) is closed upon holder base (20), e.g., as shown in FIGS. 22B and 22E. In certain embodiments, the holder top assembly comprises a top cover (23) comprising markings to show proper positioning of a rotatable handle for locking (and unlocking the closed holder, e.g., as shown in FIG. 22A, showing locked position (23a) and unlocked position (23b). In certain embodiments, holder top assembly (21) comprises a top (21a) comprising flange features (21b), wherein the top (21b) is rotated by twisting of handle (24), e.g., to engage with mated flange features on holder base (2). In preferred embodiments, a top cover (23) does not rotate upon rotation of handle (24) and top (21b).

In certain embodiments, the top assembly (21) comprises a locking feature that prevents accidental opening of the enclosing container, e.g., during agitation or transportation to and from an agitating device such as an homogenizer. In an embodiment shown in FIG. 22B, handle (24) comprises a locating pin (29) that fits into a locating hole (33) in top cover (23) of lid assembly (21) when handle (24) is moved to lock the top assembly (21) in a closed position. In preferred embodiments, lid assembly (21) further comprises a releasing feature to disengage the locking feature. For example, in the embodiment shown in FIG. 22A, handle (24) comprises a release button (25) that withdraws locating pin (29) from locating hole (33), thereby enabling the handle to rotate from the locked position (23a) into unlocked position (23b), said rotation also serving to disengage the mated flange features of the top assembly and the holder base. In some embodiments, a release button (25) is configured with a spring (34) to maintain the release button in an unreleased position until it is actuated or pressed. A release button is not limited to any particular configuration or size. In certain preferred embodiments, the release button covers a substantial portion the top of handle (24), e.g., so that it is readily actuatable by gripping handle (24), and so it is not actuated by pressure from below the handle, as might occur, e.g., when a locked enclosing container is lifted via the handle (24), e.g., for removal from an homogenizer/shaker device, or for transport.

In some embodiments, an enclosing holder comprises a lid-engaging feature (31) configured to engage with lid (2) of a sealed container within the enclosing holder. For example, in some embodiments, the interior of the holder top assembly (21) comprises lid engaging features (31) that engage crossed gripping features (4a) on lid (2), as exemplified in the container shown in FIG. 1. In preferred embodiments, the combination of the lid engaging features (31) and the sample adaptor (32) are configured to restrict or prevent any movement, e.g., rotation, of lid (2) relative to bucket (1) of the sealed container when the sealed container is secured inside a closed enclosing holder. In some embodiments, the process of securing the top assembly of the enclosing holder to the base of the enclosing holder, e.g., by turning a handle into a closed and locked position, applies a rotational pressure on lid (2) relative to bucket (1) such that lid (2) is further tightened onto the bucket (1).

In some embodiments, an enclosing holder comprises a port or valve for altering the gas contents of a closed enclosing holder. For example, in some embodiments, it is useful to create a negative pressure within the holder as a means of preventing out-flow of contents in the event of a leak, while in other embodiments, it is useful to vent pressure, e.g., pressure arising from an increase in temperature within the sealed enclosing holder. In some embodiments, it may be useful to introduce a particular gas, e.g., an inert gas such as nitrogen, into the vessel. To facilitate the movement of gases into or out of sealed enclosing holder without opening the vessel, in certain preferred embodiments, the enclosing holder comprises a suitable valve, e.g., a Schrader valve (36), for adding or removing gas (e.g., air, nitrogen) from the enclosing holder when the enclosing holder is in a closed, e.g., locked, configuration.

In some embodiments, an enclosing holder is configured to apply pressure to the bottom and/or the top of the sealed container, e.g., to limit any motion of the sealed container within the enclosing holder, and/or to support or reinforce the seal between the bucket (1) and lid (2) within the enclosing holder. For example, in some embodiments, a sample adaptor within the base of an enclosing holder, e.g., sample adaptor (32) in holder base (20) as shown in the embodiment in FIG. 22B, is mounted on compression springs (35) that maintain a compressive pressure upon the sealed container that is within a closed enclosing holder. In preferred embodiments, the enclosing holder provides pressure in alignment with a central axis of the sealed container, so as to press lid (2) toward bucket (1), and vice versa.

In some embodiments, the enclosing holder is provided with one or more gripping features, to facilitate handling and manipulating the holder, e.g., to facilitate the processes of locking and unlocking the holder. For example, in some embodiments, the enclosing holder comprises a grippable side handle (30), e.g., as shown in FIG. 22A.

The enclosing holder is preferably constructed of unbreakable material, selected to withstand vigorous shaking, rotation, or other agitation used, e.g., in homogenizing a sample in a sealed sample container. For example, in preferred embodiments, the holder base (20) comprises or is composed of metal, e.g., stainless steel, aluminum, titanium, while in other embodiments, the base comprises or is composed of plastic. In particularly preferred embodiments, holder base (20) and/or top (21a) are composed of stainless steel. Side handle (30) and hinge parts (27,28) may be composed of the same materials as each other and as the holder base, or different materials. In preferred embodiments, the side handle (30) and hinge parts (27,28) are all metal, and in particularly preferred embodiments, they all comprise or are composed of aluminum.

The holder top assembly (21) may comprise metal, plastic, rubber, silicone and/or other suitable materials. In certain preferred embodiments, the holder top assembly (21) comprises a top cover (23), handle (24), and/or the release button (25) comprise or are composed of polyoxymethylene, e.g., DELRIN®. The holder top assembly (21) preferably comprises a silicon gasket and locating pin of metal, e.g., stainless steel. Top (21a) having flange features (21b), e.g., as shown in FIG. 22D, is preferably metal, and particularly preferably stainless steel.

Holder top assembly (21) further comprises one or more lid-engaging features and a means for holding a gasket. In some embodiments, the holder top assembly is provided with a gasket holder (22) that also comprises lid engagement feature(s) (31), as shown in FIG. 22E. In certain preferred embodiments, gasket holder (22) comprises or is composed of DELRIN® plastic.

The technology finds use in kits comprising embodiments of the devices described and, in some embodiments, optional components such as, e.g., an instruction for use (e.g., providing the steps of a related method) and any related packaging for storage, shipping, and the like. Embodiments of the kits may comprise one or more solutions, e.g., comprising a stabilizing reagent, a buffer, a salt, or a preservative for using with (e.g., for treating, homogenizing, preserving, or storing) the collected specimen and the analytes it contains. Kits may also comprise other components useful for depositing a stool sample, such as a bracket or other device or hardware for mounting the bucket on or in a commode or toilet, or a separate device for conveniently securing a stool sample from subject (e.g., a paper or plastic bowl; a bag or other receptacle to fit to a commode or toilet), such that the sample may be collected, e.g., during use of a commode, and transferred to the device of the present invention. In some embodiments, a stool sample may be transferred to the device from an initial receptacle, while in some embodiments, the initial receptacle may be placed within a container of the present invention, along with the stool sample.

In yet other embodiments, a kit may comprise components related to sample processing such as sampling devices, homogenizers and/or components for testing the sample, such as analysis reagents and/or detection reagents, etc.

EXAMPLE 1

As discussed above, technology herein is directed to overcoming the challenge of providing a collection container that can be reliably used and sealed by any subject in a diverse population of subjects, including subjects having conditions that may severely compromise their ability to align and/or to firmly close a container, e.g., geriatric patients. For containers that are to be transported, e.g., from a subject's home to a laboratory, using standard commercial shipping methods, it is especially important for the subject to achieve a leak-resistant seal on the container without the need for special tools or assistance. As discussed above, technology herein provides an ergonomic collection device that can be securely closed using minimum force.

Figure 15:
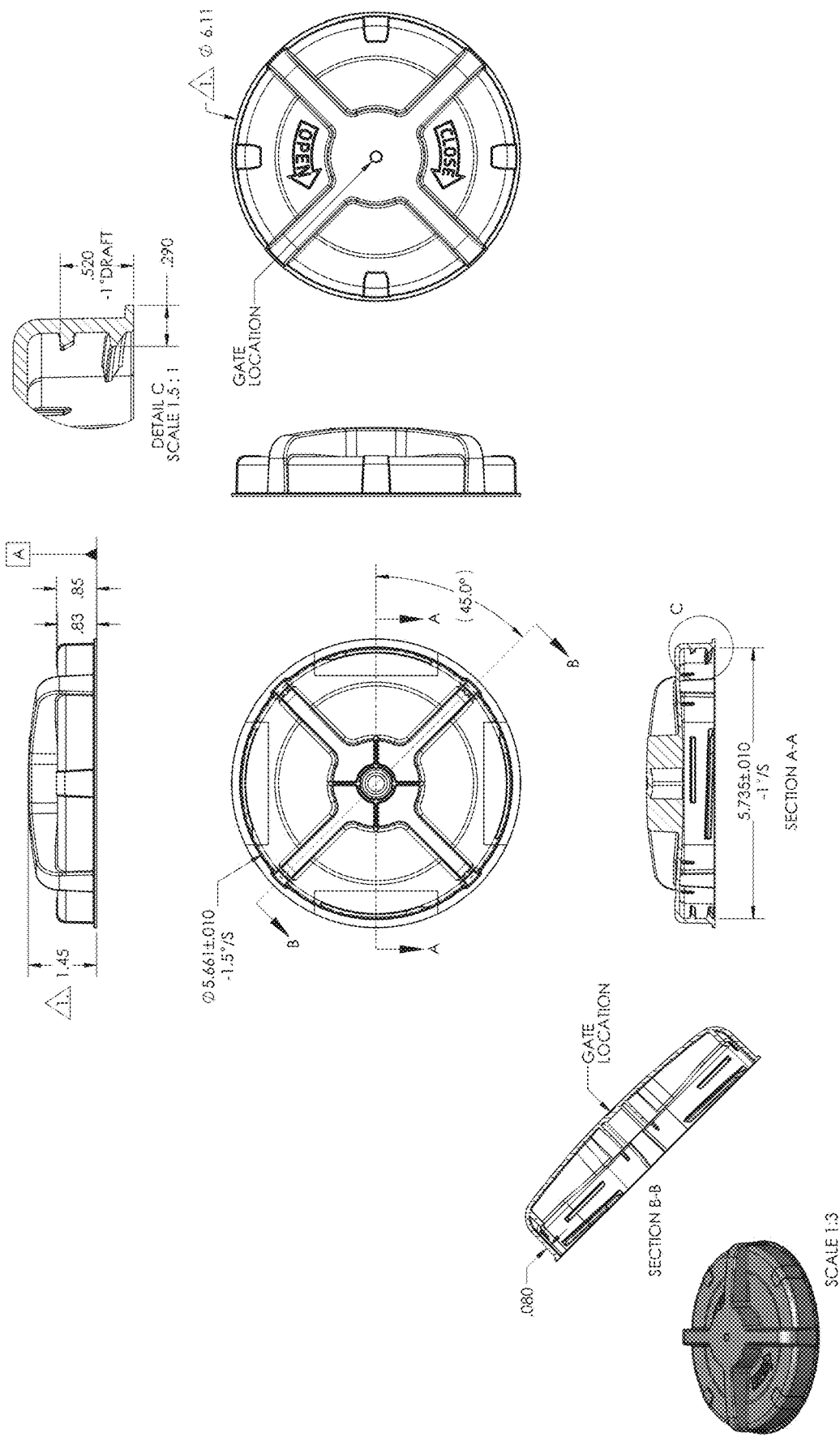
FIGS. 15A-15D show views of an embodiment of the device.
Figure 15C:
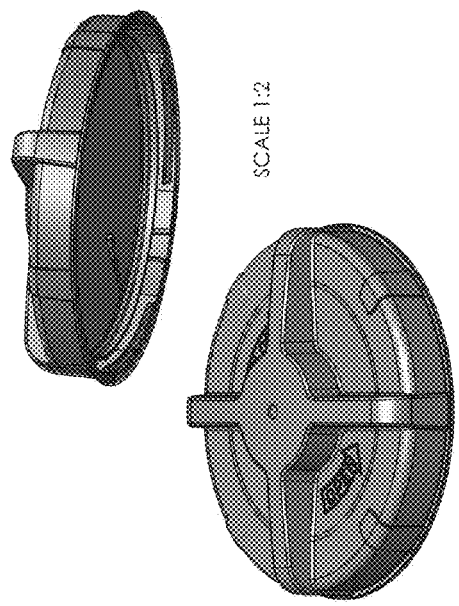
Figure 15C:
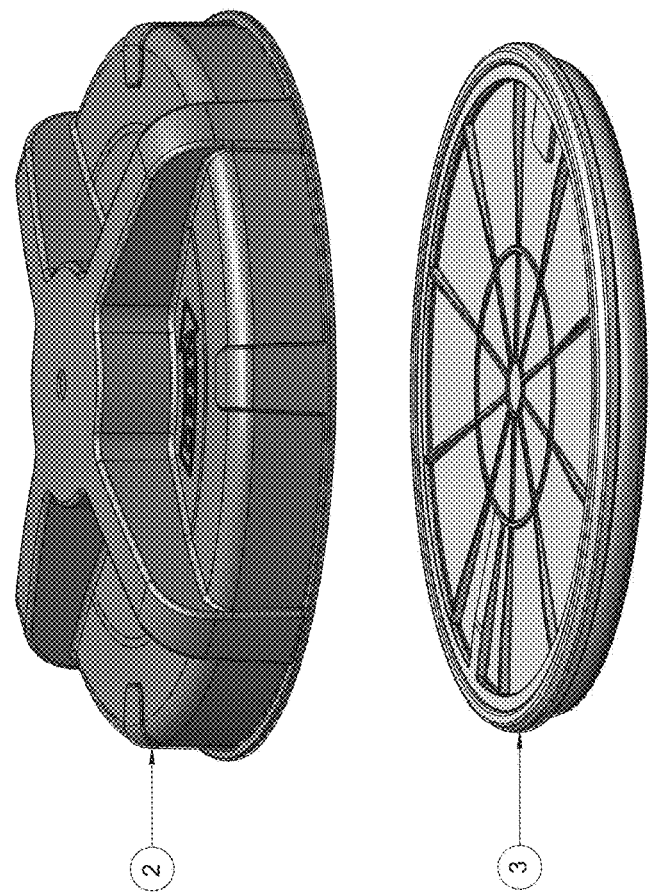
Figure 15D:
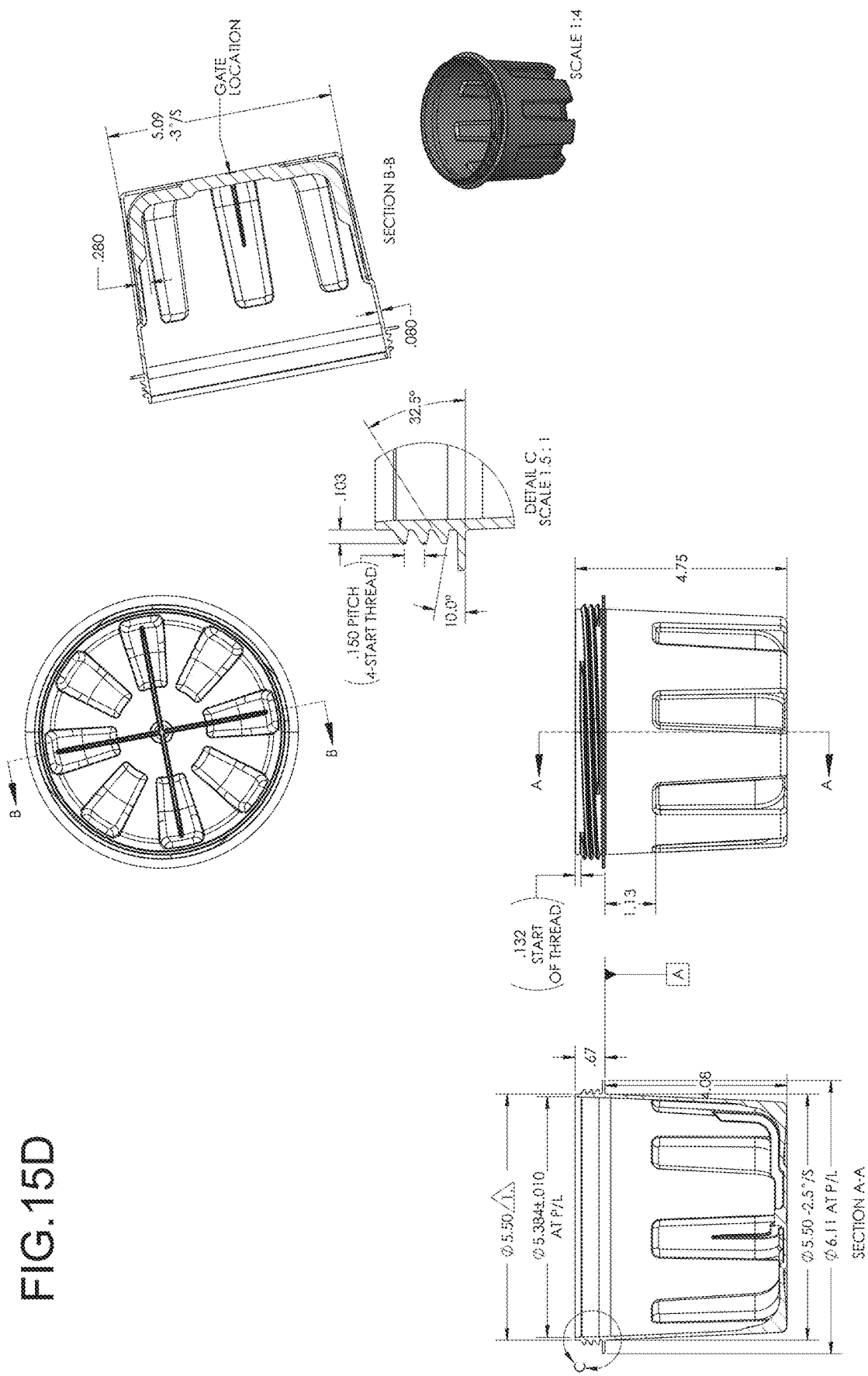

An exemplary embodiment of an ergonomic device of the present invention is shown in FIGS. 15A-D. As shown in FIG. 15D, the bucket (1) has a wide opening for receiving a stool sample. In the embodiment shown, the bucket is wider than it is tall, having a height of 4.75" and an outer diameter of 5.5" exclusive of the flange, (6.11" at the edge of the flange). The volume of the bucket is approximately 1400 mL (1.4 L).

The bucket features a series of eight gripping ridges disposed around the circumference, starting about 1.13" below a flange and extending to the base of the bucket. The sides of the bucket (at the outermost dimensions that exclude the threads and flange) are essentially straight and slightly off of parallel, with the base outer diameter being slightly smaller than the outer diameter at the top edge (5.09" vs. 5.5").

Figure 5:
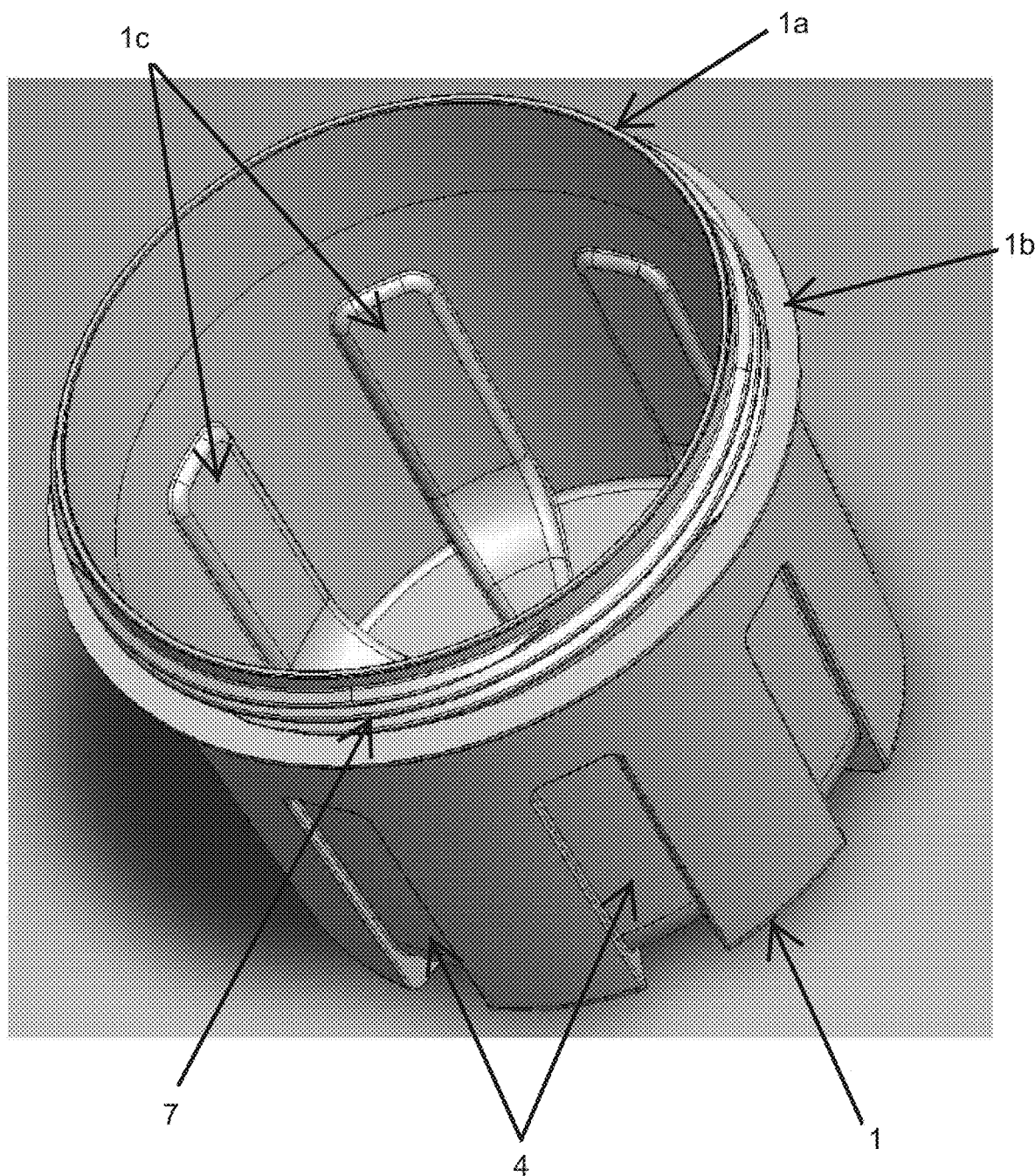
FIG. 5 is a perspective interior view of an embodiment of a bucket (1) showing a top surface (1a), gripping features (4) and an engagement portion that is a threaded portion (7). The interior of the bucket shows radially disposed ridges providing sample disruption features (1c).
Figure 6:
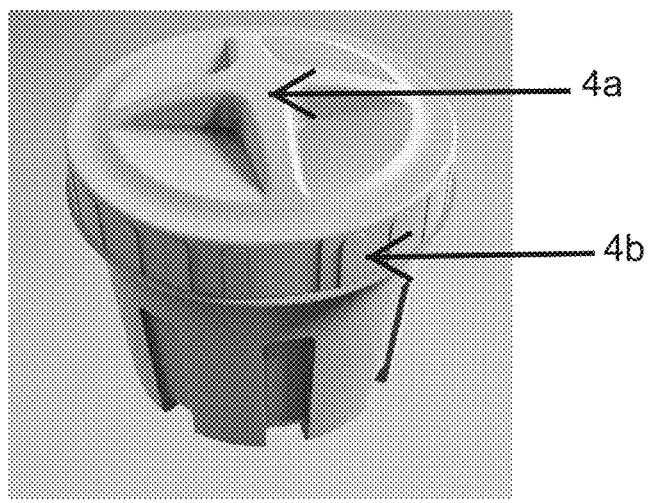
FIG. 6, panels A-C, is a drawing showing three embodiments of lids (2) having different top and edge gripping features.
Figure 6:
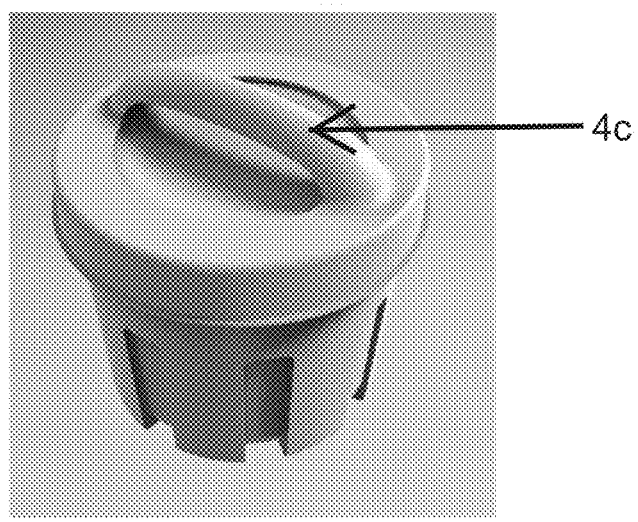
Figure 6:
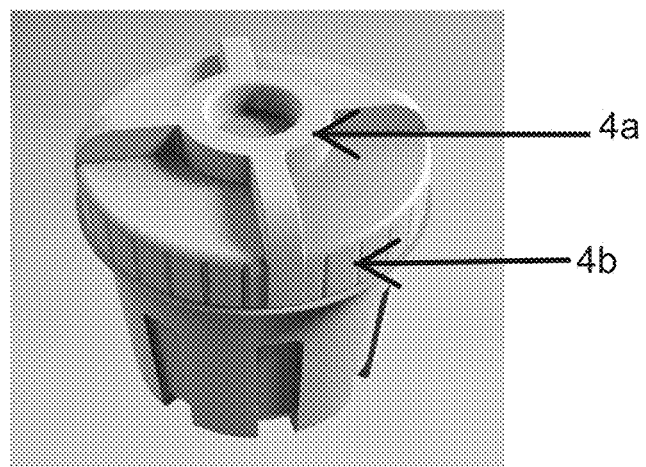
Figure 7:
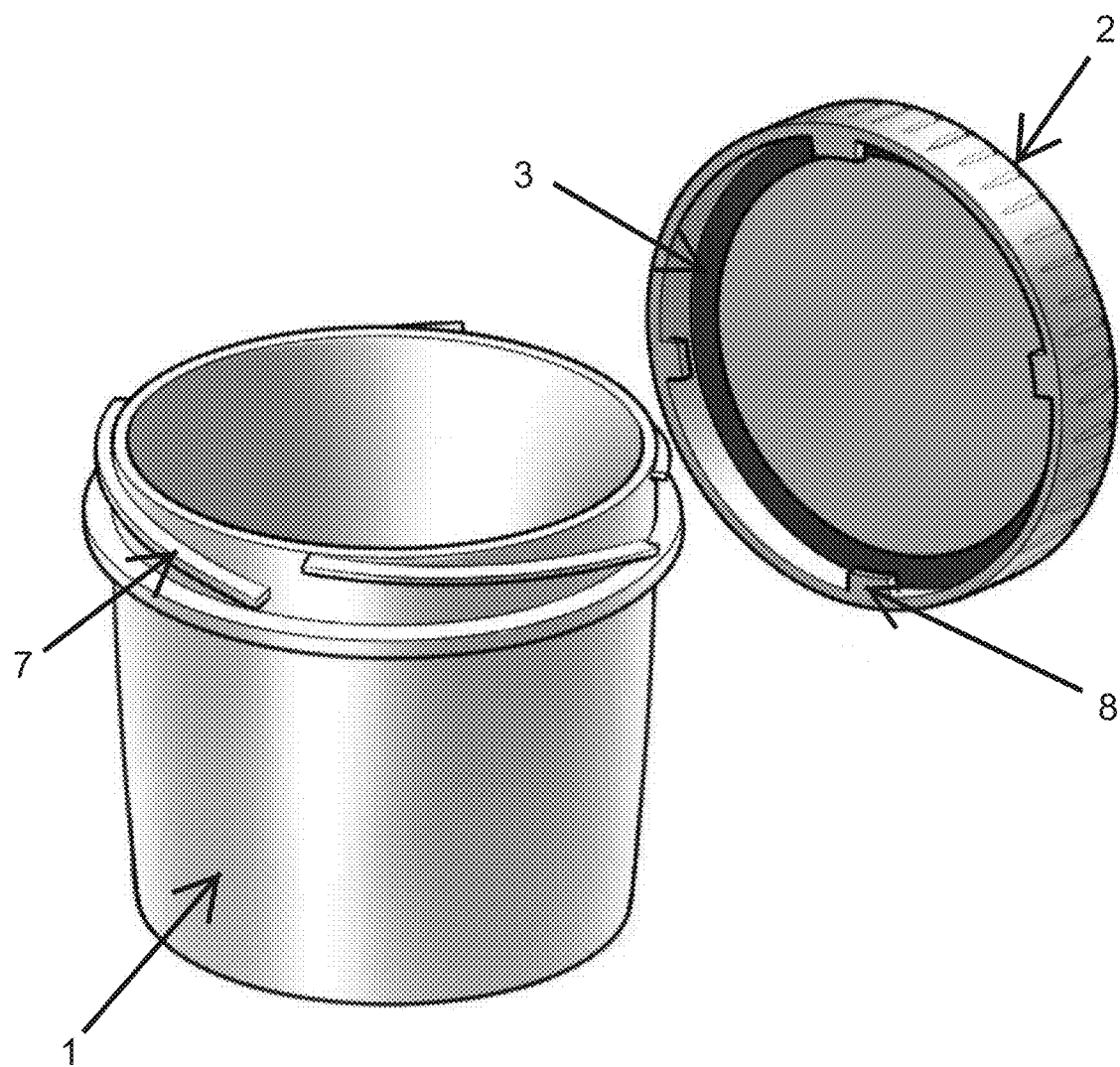
FIG. 7 is a drawing of an embodiment of a bucket (1) having a threaded engagement portion (7) and a lid (2) having a mated threaded portion (8).
Figure 8:
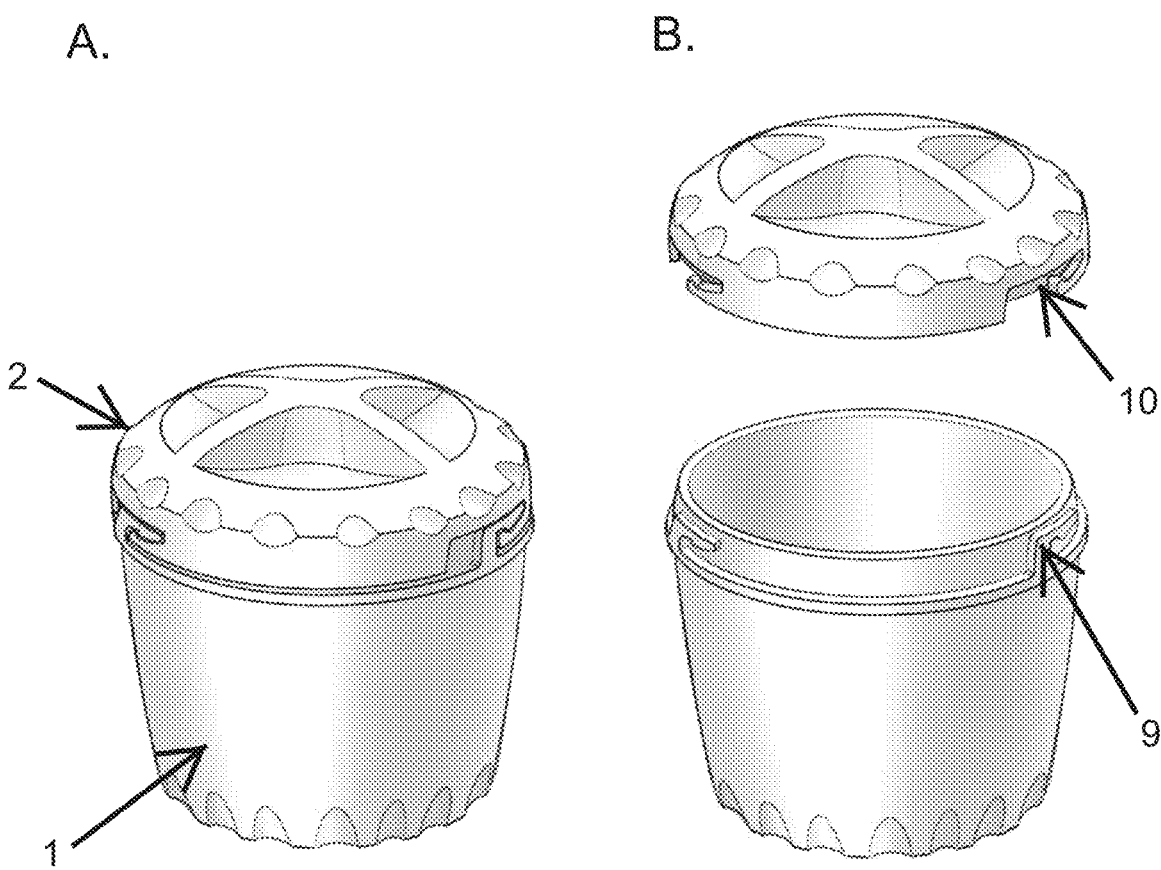
FIG. 8, panels A and B, is a drawing of an embodiment of a bucket (1) having a bayonet mount engagement portion (9) and a lid (2) having a mated bayonet mount portion (10). Panels A and B show the bucket (1) and lid (2) engaged and separated, respectively.
Figure 9:
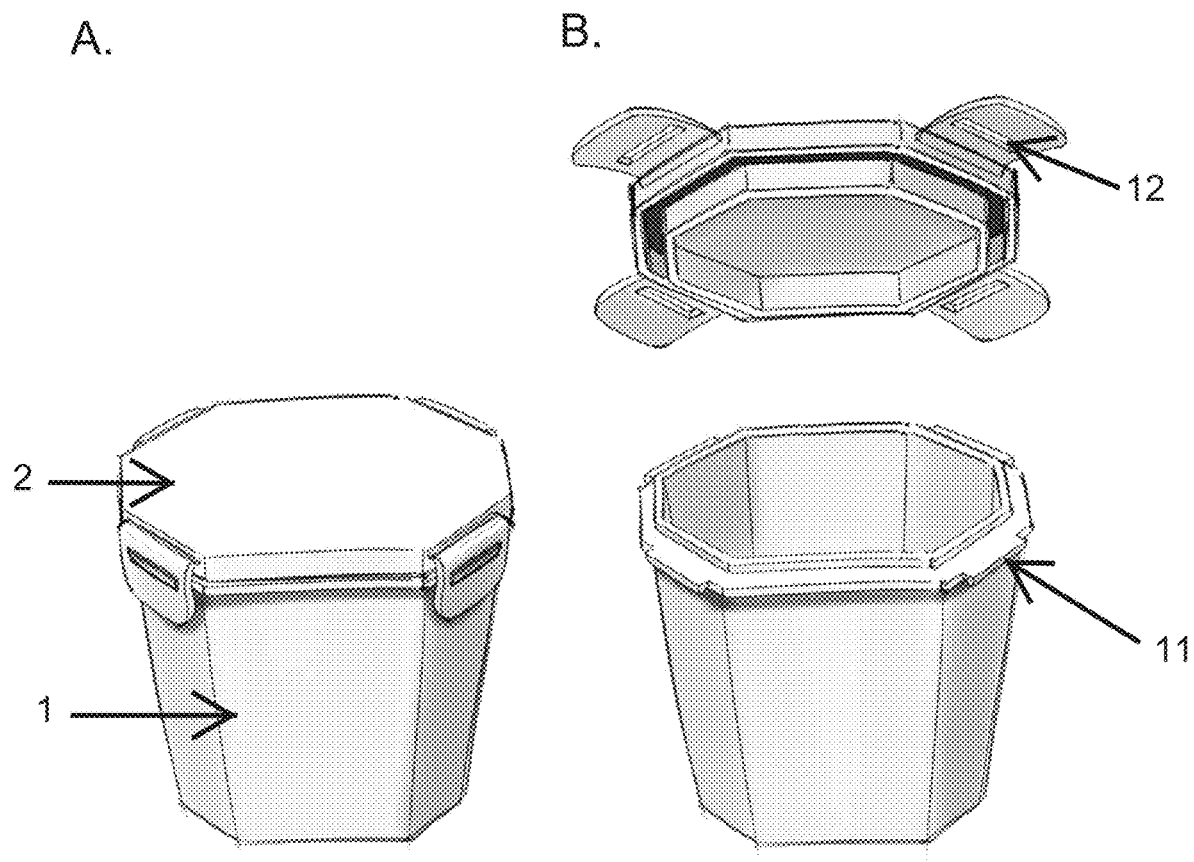
FIG. 9, panels A and B, is a drawing of an embodiment of a bucket (1) having a snap engagement portion (11) and a lid (2) having a mated snap portion (12). Panels A and B show the bucket (1) and lid (2) engaged and separated, respectively.
Figure 10:
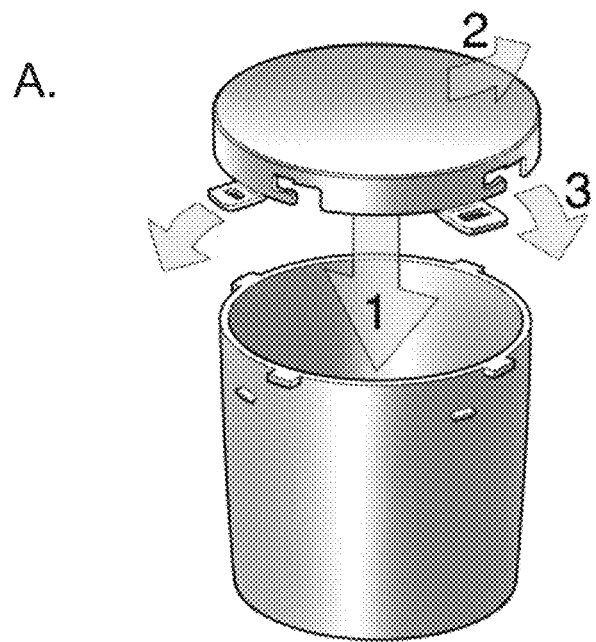
FIG. 10, panels A and B, is a drawing of an embodiment of a bucket (1) having both a bayonet mount and snap engagement features. Panels A and B show the bucket (1) and lid (2) separated and engaged, respectively.
Figure 10:
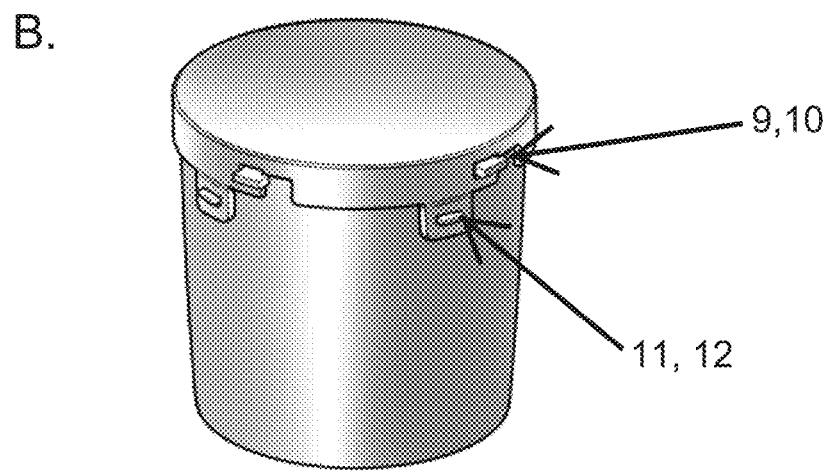

The interior of the bucket displays a series of protruding ridges that correspond to the grooves on the outside of the bucket (such as are shown in FIG. 5). Also as shown in FIG. 5, the interior side of the bucket comprises a smooth circumferential vertical surface immediately below the top edge.

As shown in FIG. 15A, the lid has a cross-shaped handle gripping feature on its top, with four arms at right angles to each other and extending from a central circular hub to the edge of the lid. The height of the gripping feature from the surface of the lid is approximately 0.6" at the hub, with each arm tapering slightly downward in height toward the edge of the lid. The lid further comprises arrows and markings indicating the direction the lid is to be turned to engage or disengage the lid from the bucket. As shown, the lid is 5.75" in diameter; 6.125" to edge of flange on its bottom edge. The lid is 0.85" high to top of body of the lid and 1.45" high to top of handle.

FIG. 15B shows a floating plate seal for use with the lid of FIG. 15A and the bucket of FIG. 15D. The floating plate is 5.62" diameter to edge of plate and has a gasket seal of 5.393" diameter. The gasket seal has a "7" shape in cross-section, such that it can contact and seal against both the top edge and interior vertical surface of the bucket. The overall height of the floating plate with the gasket is approximately 0.5". FIG. 15C shows the lid and the floating plate seal separately, and as assembled into a lid assembly ready for use, with the floating plate inside the lid.

EXAMPLE 2

The technology further provides a system wherein a sealed ergonomic container received from a user is moved directly to a processing step, such as homogenization/dispersal of the sample through agitation of the container using a mechanical shaker. The forces applied to a collection container during a mixing process may be substantial, and may further increase risk of leakage from a poorly or improperly sealed collection vessel.

For standard mechanical shakers (e.g., paint shakers, gyroscopic shakers, etc.) workers typically employ containers having particularly secure seals (e.g., the friction seals on standard paint cans) that usually must be opened using a device (e.g., a paint can opening tool, or a pry bar). Even containers having such strong friction seals typically must also be clamped to secure the seal during shaking.

In a clinical laboratory setting, it is highly desirable for a sample container to have a lid that requires neither tools nor particular physical strength to open after sample collection and/or processing. An easily removable lid, however, presents a greater risk of leakage, especially during mechanical shaking.

The leakage of even small amounts of a stool sample from a container during mixing is highly problematic. Leakage of medical samples not only poses a health and safety hazards to laboratory workers, it also increases risk of cross-contamination between patient samples, potentially compromising laboratory results.

Some mechanical shakers comprise enclosures, such as cabinets, that may limit the spread of sample that has leaked from a poorly sealed container during shaking. However, in the event of such leakage, the mechanical shaker and the cabinet interior are still contaminated, such that they cannot be used again until they have been thoroughly cleaned. Thus, even a small leak may take an entire shaker device off-line for an unacceptable length of time, disrupting work-flow.

Technology herein provides an enclosing holder that is directed toward both 1) reinforcing the integrity of the seal of a sample container during shaking, and 2) containing any sample leaking from the container such that, in the event of a leak, the mechanical shaker remains clean and usable, and contamination is contained within an article (the enclosing holder) that may be easily replaced with a clean enclosing holder, minimizing the effect of a leakage event on laboratory work-flow. Further, the contaminated enclosing holder is readily cleanable for future use.

An exemplary embodiment of an enclosing holder for an ergonomic stool collection device of Example 1 is shown in FIGS. 22A-E. FIG. 22A shows a holder base (20) having side handle (30). The holder top assembly (21) comprises a top cover (23) with markings showing the locked position (23a) and unlocked position (23b) for handle (24). Handle (24) comprises a release button (25) that disengages locating pin (29) from locating hole (33) in top cover (23) of the top assembly. The holder top assembly further comprises holder top (21a) that engages holder base (20).

FIG. 22B shows the embodiment in cross-section, showing an internal sample adaptor (32) configured to receive the ridges on the exterior of the ergonomic stool collection device of Example 1, and compression springs (35) in the holder base (20) configured to provide compressive pressure on the collection device when enclosed within the enclosing holder. Lid-engaging features (31) on the inside surface of gasket holder (22) of the holder top assembly (21) are configured to engage the cross-shaped handle gripping feature on the lid of the Example 1 container. Gasket (26) is shown positioned between the top edge of holder base (20) and the gasket holder (22) of holder top assembly (21).

Figure 22C:
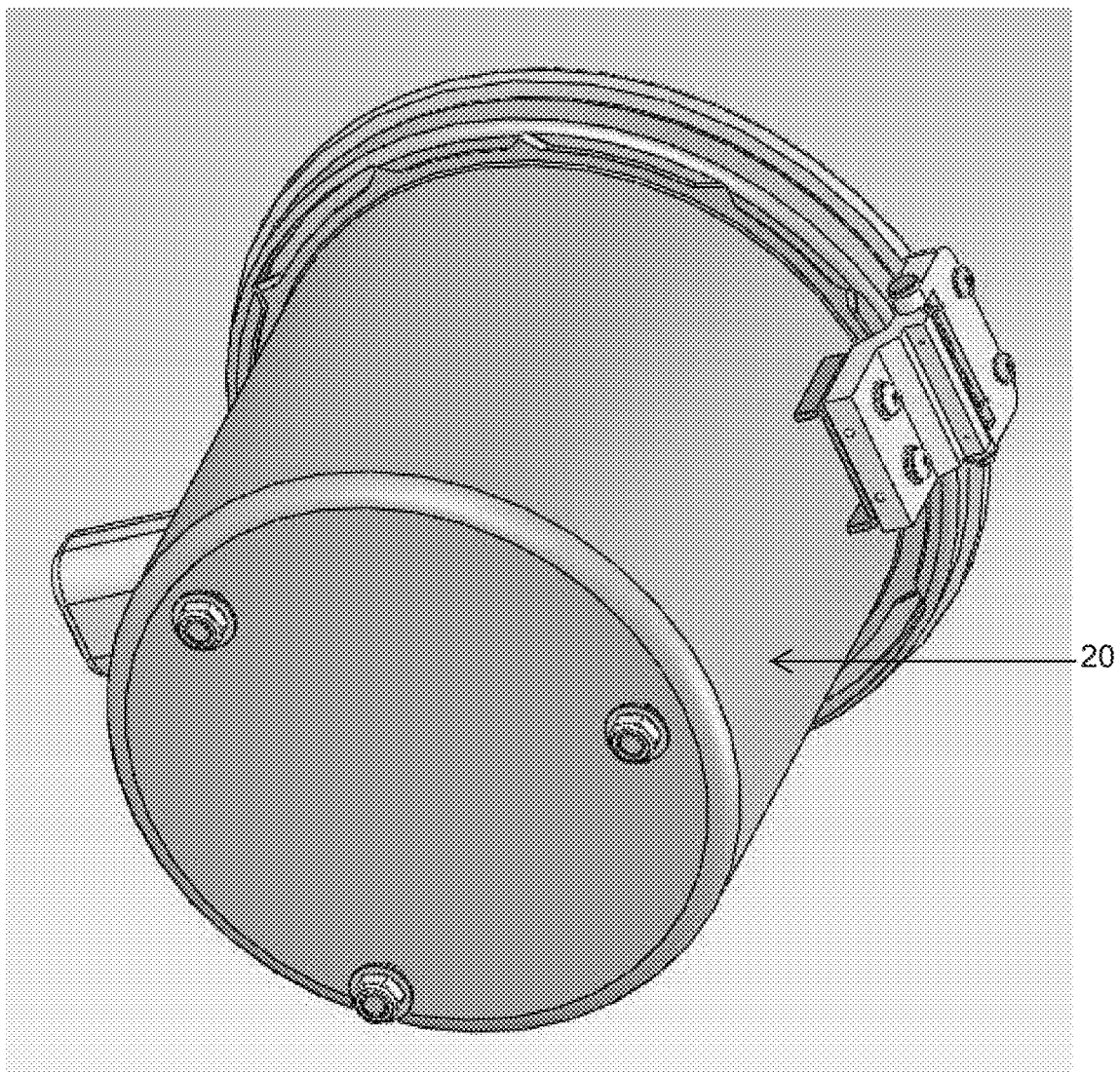
Figure 22D:
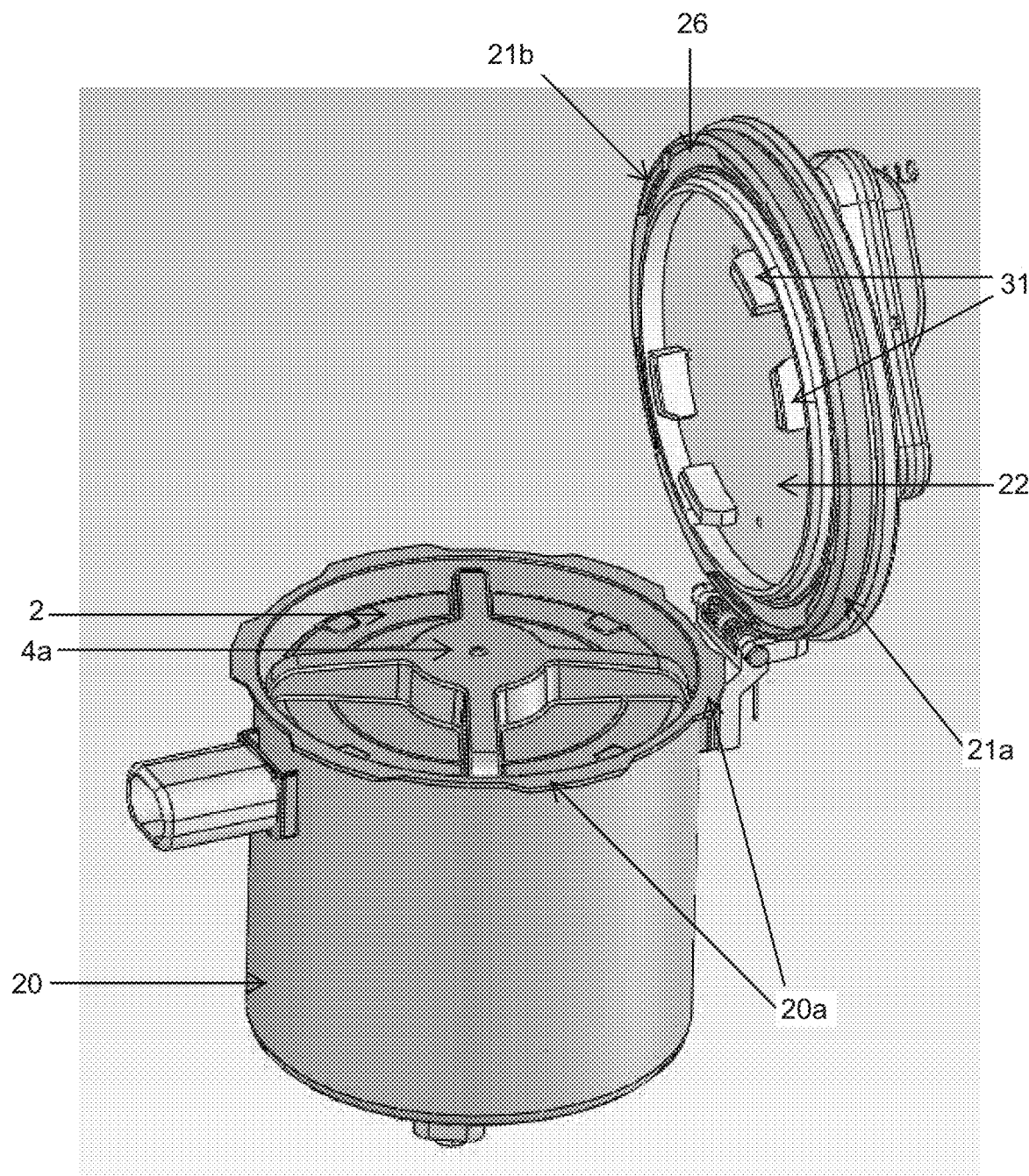
Figure 22E:
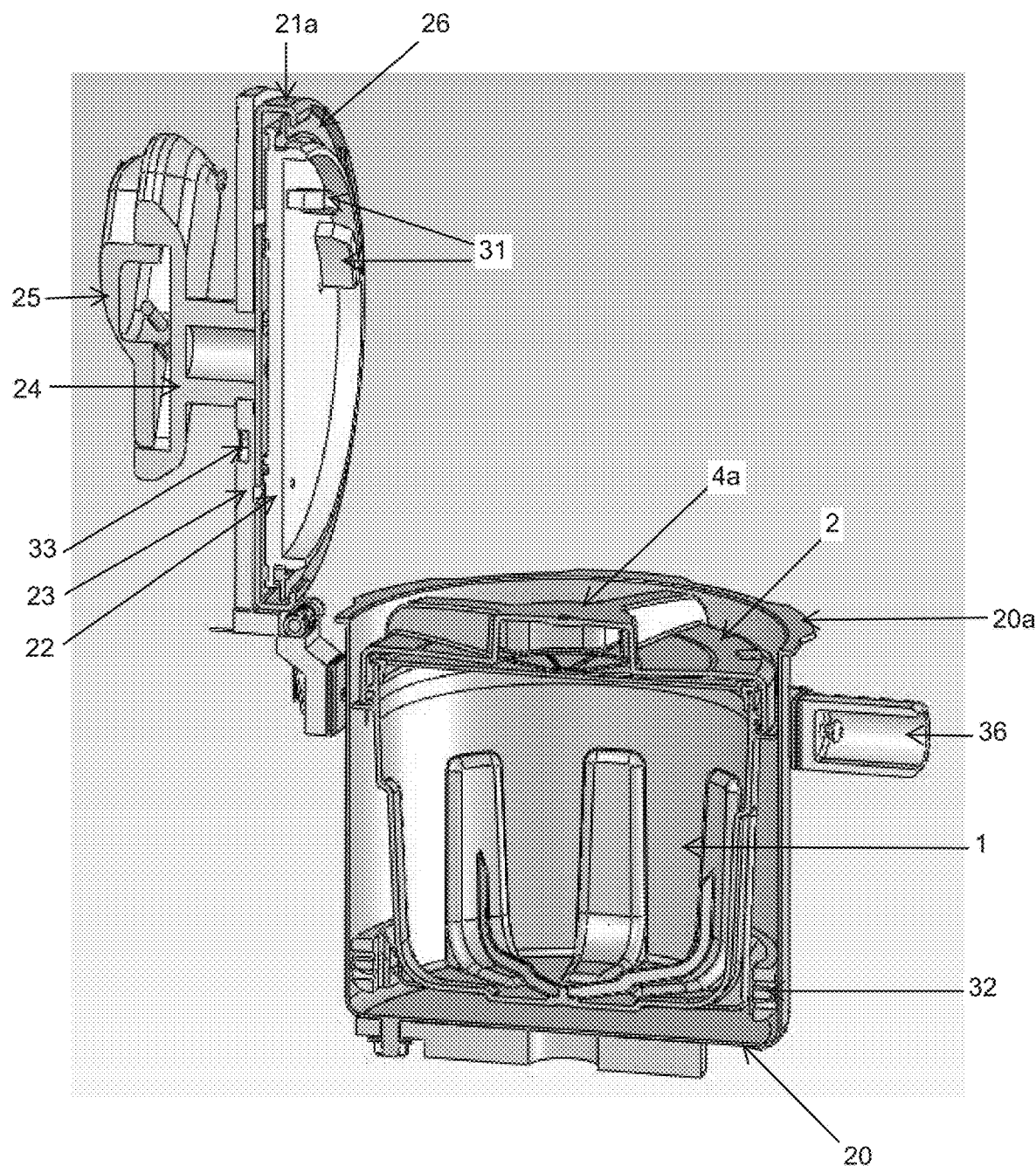

FIG. 22C shows an oblique bottom view of an enclosing holder. FIG. 22D shows an enclosing holder with the top assembly (21) in an open position with respect to holder base (20), and with an ergonomic container device as shown in FIG. 1 positioned within the base. Lid engaging features (31) on gasket holder (22) are position to engage the crossed gripping feature (4a) on lid (2) of the ergonomic device. Flanged features (20a) are shown distributed around the top of holder base (20), and are configured to engage corresponding mated features (21b) on top (21a) in holder top assembly (21). FIG. 21E shows an oblique cross-sectional view of the enclosing holder having an ergonomic container device of Example 1 positioned in it.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in engineering, material science, pharmacology, biochemistry, medical science, or related fields are intended to be within the scope of the following claims.

The invention claimed is:

1. A kit for collecting a stool specimen during use of a toilet or commode, and for containing the collected stool specimen, the kit comprising:
   a) a stool specimen collecting device having an internal volume of at least 300 ml and comprising a sample container comprising:
      a) a bucket mountable on or under a seat of a commode or toilet, the bucket comprising:
         i) a bucket bottom wall joined around a circumference to a bottom edge of a bucket side wall, a top edge of the bucket side wall circumferentially defining a top opening of the bucket having an internal diameter, and the bottom edge and top edge of the bucket side wall defining a bucket height and a vertical direction therebetween,
            wherein an interior surface of the bucket side wall defines an interior circumferential surface and an exterior surface of the bucket side wall defines an exterior circumferential surface, and
            wherein the bucket bottom wall comprises an interior surface disposed toward the top opening of the bucket;
         ii) a plurality of ridges on the exterior circumferential surface and having a length in the vertical direction, the plurality of ridges distributed radially with respect to a bucket central axis and defining grooves between adjacent ridges; and
         iii) a first threaded engagement portion; and
      b) a lid having a lid central axis, the lid comprising:
         i) a lid top wall joined around a circumference to a top edge of a lid side wall, a bottom edge of the lid side wall defining a bottom opening of the lid,
            the lid top wall comprising an interior surface disposed to the bottom opening of the lid, and an exterior surface comprising at least one raised gripping feature;
         ii) a mated threaded engagement portion removably engageable with the first threaded engagement portion of the bucket; and
         iii) a sealing plate movably retained in the lid, the sealing plate having a top surface disposed to the interior surface of the lid top wall, a bottom surface disposed toward the bottom opening of the lid, and a central axis collinear with the lid central axis, wherein the sealing plate completely covers the interior surface of the lid top wall and is rotatable with respect to the lid around the sealing plate central axis,
      wherein, when threads of the first threaded engagement portion and the mated threaded engagement portion are engaged with each other, the bucket central axis and the lid central axis are collinear, and the sealing plate seals a junction between the lid and the bucket to form a sealed sample container;
      and
   b) one or more of:
      a bracket for mounting the bucket on or under a seat of a commode or toilet to receive a stool sample deposited by a subject during use of the commode or toilet;
      a buffer solution; or
      a stool sampling device.

2. The kit of claim 1, further comprising an instruction for use.

3. The kit of claim 1, further comprising storage, shipping, or protective packaging configured to enclose a sealed sample container.

4. The kit of claim 1, wherein the buffer solution comprises a salt and a preservative or a stabilizing agent.

5. The kit of claim 4, wherein the stabilizing agent comprises a nucleic acid stabilizing agent.

6. The kit of claim 1, wherein the stool specimen collecting device has an internal volume between 300 and 1400 ml.

7. The kit of claim 1, wherein the first threaded engagement portion and the mated threaded engagement portion have threads dimensioned such that engaging the first and mated threaded engagement portions by rotation of the lid with respect to the bucket around a lid central axis to form the sealed sample container requires rotation of the lid with respect to the bucket of no more than 180 degrees.

8. The kit of claim 1, wherein the first threaded engagement portion and the mated threaded engagement portion have threads dimensioned such that engaging the first and mated threaded engagement portions by rotation of the lid with respect to the bucket around a lid central axis to form the sealed sample container requires rotation of the lid with respect to the bucket of no more than 90 degrees.

9. The kit of claim 1, wherein the stool specimen collection device further comprises a raised sample disruption feature on an interior surface of at least one of the bucket or the lid.

10. The kit of claim 9, wherein the sample disruption feature comprises one or more of a ridge or a bump.

11. The kit of claim 1, wherein the bottom surface of the sealing plate comprises a resilient compressible seating surface that is compressed around the circumference of the top opening of the bucket when the first threaded engagement portion and the mated threaded engagement portion are engaged with each other.

\* \* \* \* \*